US012650427B2

(12) United States Patent
Davis et al.

(10) Patent No.: US 12,650,427 B2
(45) Date of Patent: Jun. 9, 2026

(54) ANALYTE DETECTION WITH REDOX ACTIVE POLYMER-COATED ELECTRODE

(71) Applicants: Oxford University Innovation Limited, Oxford (GB); Universidade Estadual Paulista "Júlio De Mesquita Filho"—UNESP, São Paulo (BR)

(72) Inventors: Jason John Davis, Oxford (GB); Paulo Roberto Bueno, São Paulo (BR)

(73) Assignees: Oxford University Innovation Limited, Oxford (GB); Universidade Estadual Paulista "Júlio De Mesquita Filho"—UNESP, São Paulo (BR)

( * ) Notice: Subject to any disclaimer, the term of this patent is extended or adjusted under 35 U.S.C. 154(b) by 886 days.

(21) Appl. No.: 17/795,991

(22) PCT Filed: Jan. 29, 2021

(86) PCT No.: PCT/GB2021/050207
§ 371 (c)(1),
(2) Date: Jul. 28, 2022

(87) PCT Pub. No.: WO2021/152320
PCT Pub. Date: Aug. 5, 2021

(65) Prior Publication Data
US 2023/0081940 A1 Mar. 16, 2023

(30) Foreign Application Priority Data

Jan. 29, 2020 (GB) ...................................... 2001239
Oct. 14, 2020 (GB) ...................................... 2016287

(51) Int. Cl.
*G01N 33/543* (2006.01)
*G01N 27/22* (2006.01)
*G01N 33/68* (2006.01)

(52) U.S. Cl.
CPC ....... *G01N 33/5438* (2013.01); *G01N 27/227* (2013.01); *G01N 33/6872* (2013.01); *G01N 2333/4737* (2013.01)

(58) Field of Classification Search
CPC .............. G01N 27/026; G01N 27/227; G01N 33/5438; G01N 33/6872; G01N 2333/4737
See application file for complete search history.

(56) References Cited

U.S. PATENT DOCUMENTS

| 10,309,918 B2 | 6/2019 | Davis et al. |
| 10,309,921 B2 | 6/2019 | Bansali et al. |
| (Continued) | | |

FOREIGN PATENT DOCUMENTS

| CN | 102520187 | 6/2012 |
| CN | 106324057 | 1/2017 |
| (Continued) | | |

OTHER PUBLICATIONS

Aissa, Sondes Ben, et al. "Design of a redox-active surface for ultrasensitive redox capacitive aptasensing of aflatoxin M1 in milk." Talanta 195 (2019): 525-532. (Year: 2019).*
(Continued)

*Primary Examiner* — Robert J Eom
(74) *Attorney, Agent, or Firm* — Klarquist Sparkman, LLP

(57) ABSTRACT

The present invention relates to the electrochemical detection of an analyte by capacitance spectroscopy using a redox active polymer-coated electrode such as a polyaniline-coated electrode.

14 Claims, 15 Drawing Sheets

(56) References Cited

U.S. PATENT DOCUMENTS

2015/0147747 A1    5/2015  Cho
2017/0370867 A1*  12/2017  Davis ................ G01R 27/2605

FOREIGN PATENT DOCUMENTS

WO        WO01/61053     8/2001
WO        WO2015/022483  2/2015
WO        WO2016/120606  8/2016
WO        WO2019/145706  8/2019

OTHER PUBLICATIONS

Kulikova, T. N., et al. "Electrochemical Aptasensor with Layer-by-layer Deposited Polyaniline for Aflatoxin M1 Voltammetric Determination." Electroanalysis 31.10 (2019): 1913-1924. (Year: 2019).*
Nautiyal, Amit, Jonathan E. Cook, and Xinyu Zhang. "Tunable electrochemical performance of polyaniline coating via facile ion exchanges." Progress in Organic Coatings 136 (2019): 105309. (Year: 2019).*
Zhang, Yao, et al. "Capacitive sensing of glucose in electrolytes using graphene quantum capacitance varactors." ACS applied materials & interfaces 9.44 (2017): 38863-38869. (Year: 2017).*
Ribeiro, W. C., et al. "Molecular conductance of double-stranded DNA evaluated by electrochemical capacitance spectroscopy." Nanoscale 8.16 (2016): 8931-8938. (Year: 2016).*
Baradoke et al., "Reagentless Redox Capacitive Assaying of C-Reactive Protein at a Polyaniline Interface," Analytical Chemistry 92:3508-3511, 2020.
Baradoke et al., "Introducing polymer conductance in diagnostically relevant transduction," Biosensors and Bioelectronics 172:112705 (4 pages), 2021.
Bedatty Fernandes et al., "Label free redox capacitive biosensing," Biosensors and Bioelectronics 50:437-440, 2013.
Betty, "Highly sensitive capacitive immunosensor based on porous silicon-polyaniline structure: Bias dependence on specificity," Biosensors and Bioelectronics 25:338-343, 2009.
Bueno et al., "Capacitance Spectroscopy: A Versatile Approach to Resolving the Redox Density of States and Kinetics in Redox-Active Self-Assembled Monolayers," The Journal of Physical Chemistry B 116:8822-8829, 2012.
Bueno et al., "Measuring Quantum Capacitance in Energetically Addressable Molecular Layers," Analytical Chemistry 86:1337-1341, 2014.
Bueno et al., "Elucidating Redox-Level Dispersion and Local Dielectric Effects within Electroactive Molecular Films," Analytical Chemistry 86:1997-2004, 2014.
Dey et al., "Mediator free highly sensitive polyaniline-gold hybrid nanocomposite based on immunosensor for prostate-specific antigen (PSA) detection," Journal of Materials Chemistry 22:14763-14772, 2012.

Fernandes et al., "Comparing label free electrochemical impedimetric and capacitive biosensing architectures," Biosensors and Bioelectronics 57:96-102, 2014.
Geddes et al., "Surface chemical activation of quartz crystal microbalance gold electrodes—analysis by frequency changes, contact angle measurements and grazing angle FTIR," Thin Solid Films 260:192-199, 1995.
Goud et al., "A review on recent developments in optical and electrochemical aptamer-based assays for mycotoxins using advanced nanomaterials," Microchimica Acta 187:29 (32 pages) 2020.
International Search Report and Written Opinion from International Application No. PCT/GB2021/050207 dated Jun. 18, 2021 (18 pages).
Kaushik et al., "Mediator and label free estimation of stress biomarker using electrophoretically deposited $Ag^@AgO$-polyaniline hybrid nanocomposite," Biosensors and Bioelectronics 50:35-41, 2013.
Kim et al., "Redox-Active Polymers for Energy Storage Nanoarchitectonics," Joule 1:739-768, Dec. 20, 2017.
Li et al., "Disposable Immunochips for the Detection of Legionella pneumophila Using Electrochemical Impedance Spectroscopy," Analytical Chemistry 84:3485-3488, 2012.
Maalouf et al., "Label-Free Detection of Bacteria by Electrochemical Impedance Spectroscopy: Comparison to Surface Plasmon Resonance," Analytical Chemistry 79:4879-4886, 2007.
Malhotra et al., "Prospects of conducting polymers in biosensors," Analytica Chimica Acta 578:59-74, 2006.
Mawad et al., "A conducting polymer with enhanced electronic stability applied in cardiac models," Science Advances 2:e1601007 (14 pages), 2016.
Pan et al., "Hierarchical nanostructured conducting polymer hydrogel with high electrochemical activity," Proceedings of the National Academy of Sciences (PNAS) 109(24):9287-9292, Jun. 12, 2012.
Peng et al., "Quantification of Ionic Diffusion in Lead Halide Perovskite Single Crystals," ACS Energy Letters 3:1477-1481, 2018.
Piccoli et al., "Redox Capacitive Assaying of C-Reactive Protein at a Peptide Supported Aptamer Interface," Analytical Chemistry 90:3005-3008, 2018.
Sai et al., "Immobilization of Antibodies on Polyaniline Films and Its Application in a Piezoelectric Immunosensor," Analytical Chemistry 78:8368-8373, 2006.
Scholle et al., "Sequence of the mglB gene from Escherichia coli K12: Comparison of wild-type and mutant galactose chemoreceptors," Molecular and General Genetics 208(1-2):247-253m Jun. 1987.
Search Report from related GB Application No. GB2001239.3 dated Jul. 10, 2020 (2 pages).
Shoaie et al., "Electrochemical sensors and biosensors based on the use of polyaniline and its nanocomposites: a review on recent advances," Microchimica Acta 186:465 (29 pages), 2019.
Singal et al., "Electrochemical Impedance Analysis of Biofunctionalized Conducting Polymer-Modified Graphene-CNTs Nanocomposite for Protein Detection," Nano-Micro Letters 9:7 (9 pages), 2017.

* cited by examiner t = 0 min
Angle = 125.70 degrees t = 1 min
Angle = 123.97 degrees t = 2.5 min
Angle = 112.78 degrees t = 5 min
Angle = 77.35 degrees t = 10 min
Angle = 65.09 degrees t = 20 min
Angle = 60.99 degrees t = 40 min
Angle = 56.33 degrees t = 80 min
Angle = 43.05 degrees Angle = 125.70 degrees Angle = 43.05 degrees Fig. 9
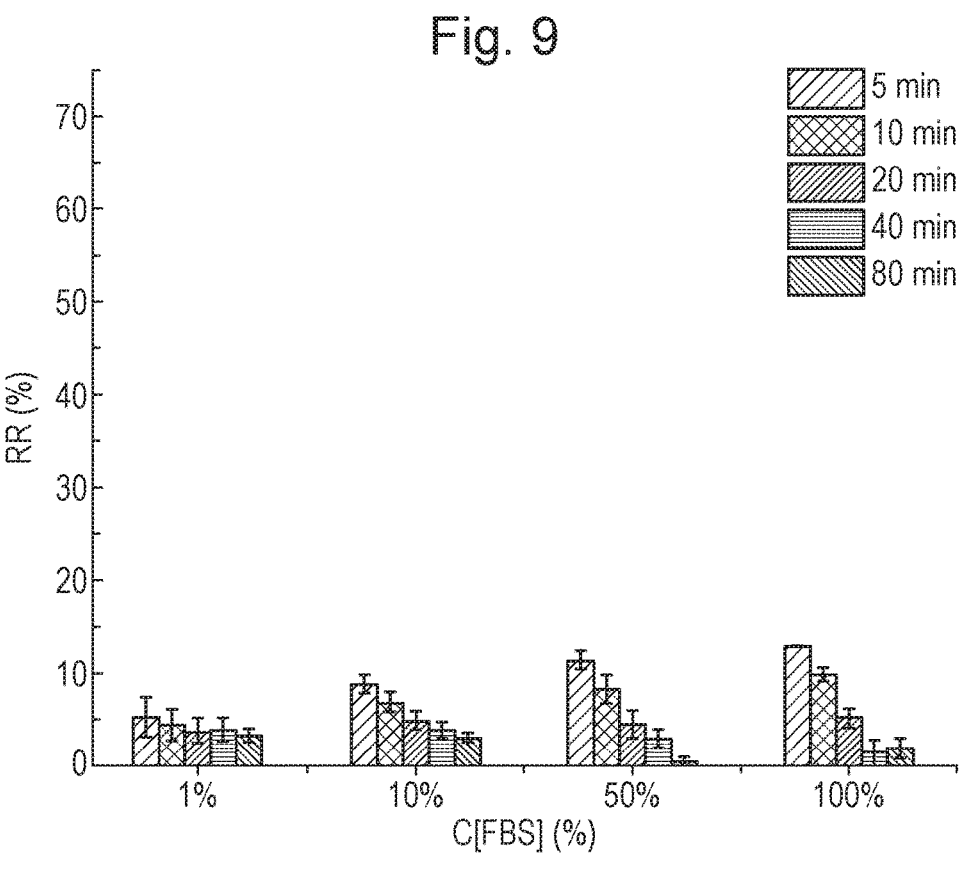
Fig. 10(a)
Fig. 10(b)
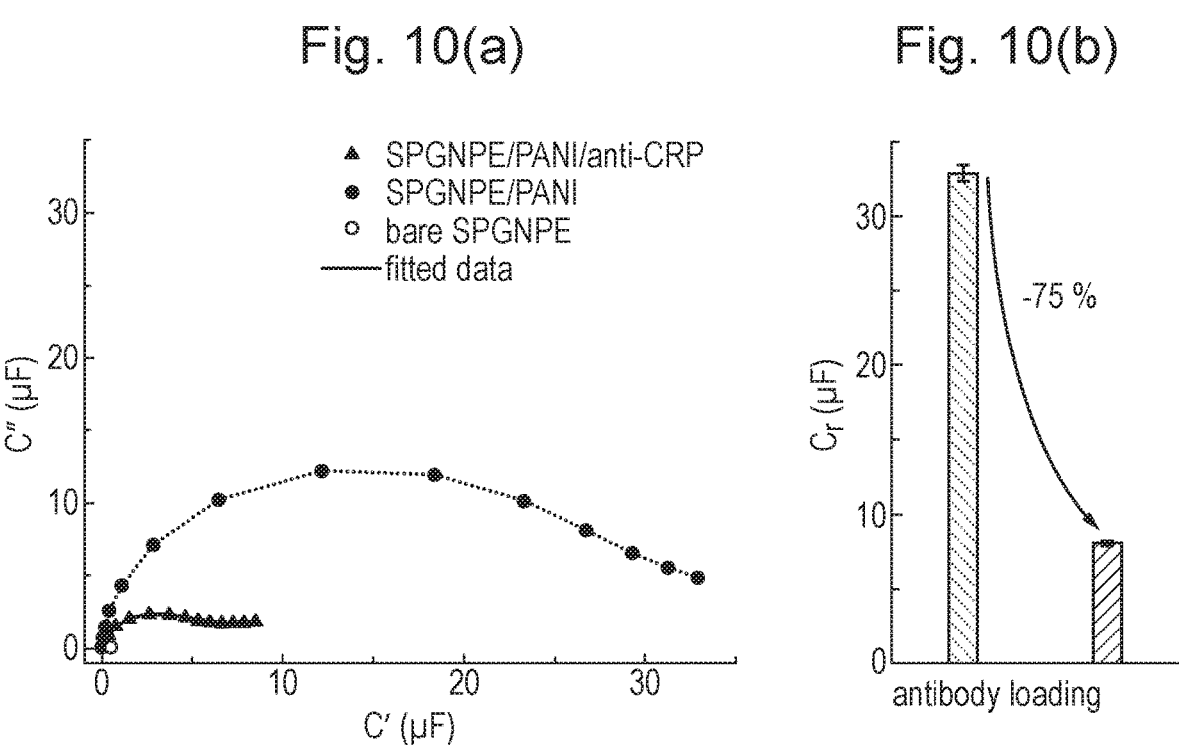

ANALYTE DETECTION WITH REDOX ACTIVE POLYMER-COATED ELECTRODE

CROSS REFERENCE TO RELATED APPLICATIONS

This is the U.S. National Stage of International Application No. PCT/GB2021/050207, filed on Jan. 29, 2021, which in turn claims the benefit of Application No. GB2001239.9 filed on Jan. 29, 2020 and Application No. GB2016287.1 filed on Oct. 14, 2020. These priority applications are incorporated herein in their entireties.

The present invention relates to the electrochemical detection of analyte species by capacitance spectroscopy using a redox active polymer-coated electrode such as a polyaniline-coated electrode.

BACKGROUND

Electrochemical techniques have been used in a broad range of sensing applications, for example for the detection and quantification of molecules of diagnostic interest in physiological samples, for sensing toxic gases and for monitoring changes in environmental parameters such as humidity.

Electrochemical impedance spectroscopy (EIS) is a technique that monitors changes in capacitance or charge-transfer resistance associated with the changes in the local environment of a suitably modified electrode surface. Such changes can include the binding of substances (e.g. of a target species such as a biomarker) to the electrode surface. EIS is an attractive technique for sensing applications in view, for example, of its constructional simplicity, sensitivity, selectivity and ready applicability within label-free methodologies.

In recent work it has been shown that electrochemical impedance methods can be applied to resolve a range of charge fluctuations within molecular films confined at electrode surfaces. These comprise changes associated with electronic dipole fluctuation and field induced ionic movement and can be resolved by Electroactive Capacitance Spectroscopy (ECS; also known as Electroactive Monolayer Capacitance Spectroscopy) according to their specific timescales and surface potential dependence. When these molecular films contain a moiety with orbital states that are energetically accessible (redox active), the electron transfer that results to/from the underlying metallic electrode generates a new, and sensitively potential dependent, charging process at this interface. This faradaic capacitance (known as redox capacitance, $C_r$) is not only electrostatic and can be (for high quality molecular films with associated fast rates of heterogeneous electron transfer) hundreds of times greater than the Helmholtz contribution. It has been shown that this $C_r$ signature can be integrated into films which are additionally able to recruit specific targets of interest (such as the antigen partners of antibodies or aptamers). The redox capacitance change can then be used in the establishment of a novel label free biosensing format of high sensitivity, stability and convenience. For more background details, reference can be made, for example, to WO 2015/022483, WO 2016/120606, J. Phys. Chem. B 2012, 116, 30, 8822-8829, Biosensors and Bioelectronics 50 (2013) 437-440, Biosensors and Bioelectronics 57 (2014) 96-102 and WO 2019/145706.

One critical factor affecting the performance of redox capacitance spectroscopic methods is the structure of the functionalised electrode bearing the confined molecular film. Optimisation of the electrode has the potential to yield improvements in sensor capabilities, for example for achieving enhanced limits of detection ("LOD"), sensitivity to minute changes in target species concentration, and/or selectivity to the target species of interest.

To date, sensors utilising redox capacitance spectroscopic methods have almost exclusively involved preparing electrodes with surfaces modified to contain ferrocene ("Fc") moieties that act as a redox transducer. Previous work focusing on such redox capacitance spectroscopic systems has generally not identified any particular limitations associated with this strategy for providing the required redox activity of the working electrode of the sensor apparatus.

Nonetheless, there remains a need in the art to provide further improved systems for sensing of a target species, for example that enable further improvements in features such as limit of detection ("LOD"), sensitivity to changes in target species concentration, selectivity to the target species of interest, stability of sensing and/or amenability to application of commercially desirable electrode technologies, such as application to array set-ups.

SUMMARY OF THE INVENTION

The present inventors have now identified that electrochemical sensing methods based on reagent-less redox capacitance spectroscopic detection can be substantially improved by modifying the working electrode to accommodate a film comprising a redox-active, electrically conductive polymer.

Although films of this nature, amongst a vast array of other different electrode types, have previously been used in certain electrochemical systems, including those designed for biosensing applications, particular unexpected technical advantages have been identified when applying such films to redox capacitance sensing methods. It is believed that the present application provides the first report of the use of redox-active, electrically conductive polymers for providing the intrinsic redox capacitance of the working electrode in reagent-less redox capacitive biosensing techniques.

In more detail, the applicant has now found that the use of disposed ferrocene moieties widely applied in previous redox capacitance methods can have certain disadvantages, owing for instance to the chemical instability over time of the ferrocene moieties, challenges in disposing sufficient quantities of ferrocene moieties on the electrode substrate to maximise the baseline redox capacitance signal on which the technique is founded, and limitations in the nature of the electrode substrates on which the ferrocene moieties can feasibly be disposed (to date, provision of ferrocene-functionalised working electrodes for redox capacitance sensing has only been achieved using gold substrates to provide the support for monolayers into which the ferrocene moieties are integrated). By contrast, replacing the ferrocene moieties, and the monolayers into which they are integrated, with a layer of redox-active, electrically conductive polymer has been found to give rise to at least the following advantages in the specific context of redox capacitance sensing:

Securing a more stable baseline redox capacitance signal via the enhanced chemical stability of films of redox-active, electrically conductive polymer (e.g. a polyaniline, PANI, film) compared with monolayers comprising ferrocene moieties. Such stability is highly desirable in redox capacitance sensing, which is based on intrinsically small signals and so is particularly susceptible to sources of measurement error that may be less significant in the context of other sensing arrangements.

Securing a higher baseline signal (i.e. the signal associated with redox capacitance of the electrode in the absence of target analyte species), against which decrease in signal caused by binding of the target analyte can be more readily discerned. The intrinsic redox activity of each molecular chain of the polymer disposed on the electrode substrate provides for a substantially higher redox capacitance than can typically be achieved when seeking to integrate ferrocene moieties into a monolayer surface as in the previously constructed systems.

Enabling wide applicability of the redox active surface to substantially all kinds of underlying electrode substrate. Ferrocene-based systems have typically been demonstrated to date only on gold substrates. Polymer-based systems can easily be applied to a wide variety of surfaces, notably including those commercially prepared by screen printing techniques and amenable to array (multiplexing) set-ups.

Enabling a high degree of control of film thickness, via the ease of controlling the extent of polymerisation (e.g. by electropolymerisation) of the polymer onto the underlying electrode substrate. In the context of redox capacitance spectroscopy, such ease of control of film thickness can be highly advantageous for, in any given sensing application, balancing the sensitivity of the sensor as measured by changes in redox capacitance (which, as described in more detail herein, may generally decrease with increasing polymer film thickness) as against anti-fouling properties/non-selective adsorption (which, as described in more detail herein, may generally improve with increasing polymer film thickness). The appropriate balance of these competing factors can therefore readily be optimised for any given system (associated with a specific target analyte identity, receptor structure, consequent intrinsic sensitivity, characteristic types of associated carrier media and likely potential foulant species, and so on) in a way that is significantly more challenging in the context of previous redox capacitance set-ups.

Securing a higher loading of receptors that bind the target analyte. As a result of their polymeric, three-dimensional structure, the polymers may be supportive of a higher level of receptor loading (relevant to sensor sensitivity) than ferrocene harbouring monolayers.

Specifically, the present invention therefore provides an electrochemical method of sensing a target species, which method comprises: (A) contacting a carrier medium that may comprise said target species with an electrode that comprises: (i) an electrically conductive substrate; (ii) a film comprising a redox-active, electrically conductive polymer disposed on the substrate; and (iii) at least one receptor associated with the film, wherein the receptor is capable of binding to the target species; and (B) determining, via electrochemical capacitance spectroscopy, whether the target species is present in the carrier medium.

In a related aspect, the present invention provides an electrochemical method of sensing a target species, which method comprises: (A) contacting a carrier medium that may comprise said target species with an electrode that comprises: (i) an electrically conductive substrate; (ii) a film comprising a redox-active, electrically conductive polymer disposed on the substrate; and (iii) at least one receptor associated with the film, wherein the receptor is capable of binding to the target species; and (B) determining, via electrochemically determining the conductance of the electrode, whether the target species is present in the carrier medium The present invention also provides use of an electrode for determining, via electrochemical capacitance spectroscopy and/or determining, via electrochemically determining the conductance of the electrode, whether a target species is present in a carrier medium, said electrode comprising: (i) an electrically conductive substrate; (ii) a film comprising a redox-active, electrically conductive polymer disposed on the substrate; and (iii) at least one receptor associated with the film, wherein the receptor is capable of binding to the target species.

Further preferred features and embodiments are described in the accompanying description and the appended claims.

DESCRIPTION OF THE DRAWINGS

FIG. 9 shows the change in the relative response (RR %) of Cr of PANI-PA films of different thicknesses upon subsequent incubation with increasingly concentrated fetal bovine serum (FBS) for 10 min, as described in Example 1. Error bars represent one standard deviation of three repeat measurements (incubation in same dilution) of one electrode. For each concentration of FBS, PANI-PA films are, from leftmost to rightmost, those from polymerisation for 5 min, 10 min, 20 min, 40 min and 80 min.

FIG. 10 shows capacitive Nyquist plots (panel (a)) and relative response (panel (b)) before and after anti-CRP immobilization onto PANI-10 min, as described in Example 1.

DETAILED DESCRIPTION

Figure 1:
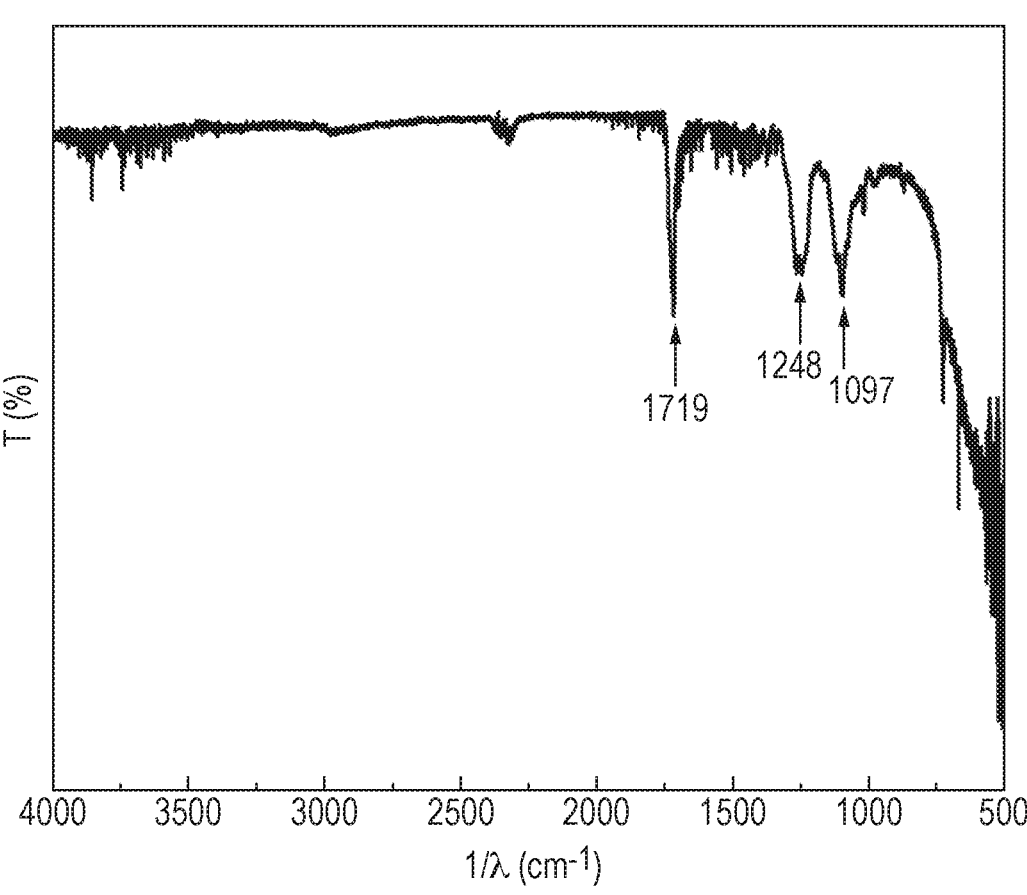
FIG. 1 shows an FT-ATR-IR spectrum of a phytic acid-doped PANI film electropolymerised for 80 min on a screen-printed graphene nanoplate working electrode (unmodified screen-printed electrodes were utilized for the background correction), as described in Example 1.

Optional and preferred features of the present invention are now described. Any of the features described herein may be combined with any of the other features described herein, unless otherwise stated.

The Electrode

The electrode functions as the working electrode in an electrochemical system, specifically a system adapted for performing electrochemical impedance spectroscopy (EIS) and more specifically still a system adapted for performing redox capacitance spectroscopy (i.e. for obtaining measurements of the redox capacitance of the system).

Electrically Conductive Substrate

The electrode comprises an electrically conductive substrate. This substrate may comprise any electrically conducting material. The substrate may comprise a metal or carbon. The metal may be a metal in elemental form or an alloy of a metal. Optionally, the whole of the substrate comprises a metal or carbon. The substrate may comprise a transition metal. The substrate may comprise a transition metal selected from any of groups 9 to 11 of the Periodic Table. The substrate may comprise a metal selected from, but not limited to, rhenium, iridium, palladium, platinum, copper, indium, rubidium, silver and gold. The substrate may comprise a metal selected from gold, silver and platinum. The substrate may comprise a carbon-containing material, which may be selected from edge plane pyrolytic graphite, basal plane pyrolytic graphite, glassy carbon, boron doped diamond, highly ordered pyrolytic graphite, carbon powder and carbon nanotubes.

In one embodiment, the substrate comprises gold, for example the substrate is a gold substrate. However, it is also possible for the substrate to comprise other materials and so, for instance, in other embodiments, the electrically conductive substrate is not a gold substrate. One advantage of utilising a redox-active, electrically conductive polymer as the redox transducer in the methods of the invention is that such polymers can readily be engineered on substantially any electrode substrate material (in contrast, it may be more difficult or not possible for other types of redox active surface layers to be accommodated on substrates other than, for instance, gold, owing to the nature of the binding of the surface layer material to the substrate material). Non-limiting further examples of suitable electrically conductive substrates include carbon (e.g., graphene), platinum, silver, ruthenium oxide and indium tin oxide (ITO). Furthermore, a specific advantage associated with the wide applicability of the polymer films is that they can readily be applied onto screen printed electrode (SPE) substrates (e.g. any of gold, carbon, platinum, silver, ruthenium oxide and ITO SPEs, for instance carbon, platinum, silver, ruthenium oxide and ITO SPEs). The electrode comprising the electrode substrate may, for instance, be one electrode in a multi-electrode array (i.e., a multiplex array).

The electrically conductive substrate in the present electrode preferably does not comprise or consist of silica, e.g. porous silica. The electrode as a whole preferably does not comprise silica, e.g. porous silica. The electrically conductive substrate also preferably does not comprise or consist of carbon nanotubes. The electrode as a whole preferably does not comprise carbon nanotubes.

The electrode surface (i.e., the substrate surface) may be, and preferably is, planar, which includes a generally flat surface, e.g. without indentations, protrusions and pores. Preferably, for instance, the electrode surface (e.g., the planar electrode surface) does not have a microchannel structure (e.g., one that feature a plurality of indentations that constitute microchannels, such as in a porous silicon electrode). Such substrate surfaces can be readily prepared by techniques such as polishing with fine particles, e.g. spraying with fine particles, optionally in a sequence of steps where the size of the fine particles is decreased in each polishing step. The fine particles may, for example, comprise a carbon-based material, such as diamond, and/or may have particles with diameters of 10 μm or less, optionally 5 μm or less, optionally 3 μm or less, optionally 1 μm or less, optionally 0.5 μm or less, optionally 0.1 μm or less. Following polishing, the substrate surface may be washed, e.g. ultrasonically, optionally in a suitable liquid medium, such as water, e.g. for a period of at least 1 minute, e.g. from about 1 minute to 10 minutes. Optionally, the substrate surface may be washed with an abrasive, e.g. acidic, solution, for example following the polishing and, if used, ultrasonic washing steps. The abrasive solution may comprise an inorganic acid, e.g. $H_2SO_4$, and/or a peroxide, e.g. $H_2O_2$, in a suitable liquid medium, e.g. water. Optionally, the substrates can be electrochemically polished, which may follow any steps involving one or more of polishing with fine particles, washing e.g. ultrasonically and/or using an abrasive solution. The electrochemical polishing may involve cycling between an upper and lower potential until a stable reduction peak is reached, e.g. an upper potential of 0.5 V or more, optionally 1 V or more, optionally 1.25 V or more, and a lower potential of 0.5 V or less, optionally 0.25 V or less, optionally 0.1 V or less.

Film Comprising Redox-Active, Electrically Conductive Polymer Disposed on the Substrate The film comprises a redox-active, electrically conductive polymer disposed on the substrate.

By "disposed on the substrate", it is preferably meant that the electrically conductive substrate and the film constitute discrete portions of the electrode, e.g. the electrode comprises a first layer that is the electrically conductive substrate and a second layer, which is different from the first layer, and that is the film comprising the redox-active, electrically conductive polymer. Typically, the electrode is not a composite electrode that comprises, in a single portion, both the electrically conductive substrate and the redox-active, electrically conductive polymer. Typically, the electrically conductive substrate (e.g., the first layer of the electrode) does not contain redox-active, electrically conductive polymer. Typically, the redox-active, electrically conductive polymer is present in the electrode solely in the film that is disposed on the substrate. In a preferred embodiment the electrode does not comprise additional electrically conductive layers other than the above first layer and second layer.

A number of redox-active, electrically conductive polymer films are, in general, known in the art (although to the applicant's knowledge they have not previously been applied to redox capacitance sensing methods, or the advantages of so-doing appreciated). In general, any redox-active, electrically conductive polymer can be used to form the film, subject to the requirements that: (a) the polymer be electrically conductive; and (b) the polymer be redox active in a potential range of practical use (e.g., one that that can be applied in redox capacitance sensing methods in a suitable experimental setup and in the presence of carrier fluids relevant to the target species of interest).

Non-limiting examples of redox-active, electrically conductive polymers known in the art include polyaniline (commonly abbreviated as "PANI"), poly(3,4-ethylenedioxy thiophene) ("PEDOT"), polythiophene ("PT"), poly(3,4-propylenedioxy thiophene) ("PProDOT"), PEDOT:poly(4-styrene sulfonate) ("PEDOT:PSS"), polypyrrole ("PPy"), polythionine (PTH) and polythiophene dopamine (PoPD).

The redox-active, electrically conductive polymer is typically both electrically conductive and chemically stable in the carrier medium. For instance, in a preferred embodiment, the redox-active, electrically conductive polymer is both electrically conductive and chemically stable in a 0.1 M phosphate buffer ("PB") solution at pH=7.4.

In a currently preferred aspect, the redox-active, electrically conductive polymer is polyaniline (PANI).

Methods for disposing the polymer film on the electrically conductive substrate are not particularly limited. For instance, methods previously applied and known in the art to functionalise electrodes with polymer films, in order to pursue different methods such as different biosensing techniques, can be applied. Without limitation, one suitable method for disposing polymer films can be via electropolymerisation (e.g., electropolymerisation of PANI). The working Examples provide a non-limiting, representative account of preparation of a polymer film by such means.

As described elsewhere herein, one advantage of conducting redox capacitance spectroscopic sensing of a target analyte using the electrode defined herein is that the thickness of the polymer film can readily be optimised so as to achieve the best balance of sensitivity (e.g., by maximising the signal response to the presence of target analyte) and selectivity (e.g., by avoiding electrode fouling with non-specific adsorption events). For instance, polymer film thickness can readily be controlled by methods well known in the art, such as controlling polymerisation (e.g. electropolymerisation) time, quantity of monomer reagent for polymer production, and so on. In an embodiment, a plurality of electrodes can be prepared featuring films of different thickness (but with other variables, such as polymer chemical structure, dopant identity and quantity, receptor identity, etc., held constant), and comparative, control redox capacitance spectroscopic methods performed to determine the best-performing electrode.

The redox-active, electrically conductive polymer typically comprises a plurality of redox active monomeric repeating units. For instance, in the redox-active, electrically conductive polymer PANI the plurality of redox active monomeric repeating units are aniline units. One means of quantifying the thickness of the film is by determining the surface coverage ($\Gamma$) of the plurality of redox active monomeric repeating units on the electrically conductive substrate. For instance, this surface coverage can be measured from the redox capacitance, $C_r$, of the electrode obtained via circuit fitting and in the presence of a control carrier medium containing no target species, as demonstrated in Example 1 of this application and described in more detail in Bueno et al. Anal. Chem. 2014, 86 (3), 1337-1341, the content of which is herein incorporated by reference in its entirety. An example of a suitable control carrier medium is a 0.1 M phosphate buffer ("PB") solution at pH=7.4. The surface coverage may, for instance, be in the range 1 to 100 $nmolcm^{-2}$, preferably 3 to 40 $nmolcm^{-2}$, more preferably still 5 to 20 $nmolcm^{-2}$ and most preferably 8 to 13 $nmolcm^{-2}$. In particular, in a preferred embodiment of the invention when the redox-active, electrically conductive polymer is PANI, the surface coverage is 1 to 100 $nmolcm^{-2}$, preferably 3 to 40 $nmolcm^{-2}$, more preferably still 5 to 20 $nmolcm^{-2}$ and most preferably 8 to 13 $nmolcm^{-2}$. As described above, the surface coverage can readily be adjusted and controlled, for instance, by controlling polymerisation (e.g. electropolymerisation) time, quantity of monomer reagent for polymer production, and so on.

Optionally, the film is doped with a dopant capable of enhancing the electrical conductivity (and/or chemical stability) of the polymer. For instance, the film may be doped with phytic acid (e.g. when the redox-active, electrically conductive polymer is polyaniline). Phytic acid doping has been previously shown to endow the PANI films with higher conductivity in physiological pH and high hydrophilicity (see, e.g.: Mawad et al. Sci. Adv. 2016, 2 (11), e1601007; and Pan et al. Proc. Natl. Acad. Sci. U.S.A. 2012, 109 (24), 9287-9292).

Preferably the film that comprises a redox-active, electrically conductive polymer and that optionally contains a dopant does not further comprise carbon nanotubes. Additionally, the film preferably does not comprise electrically conductive metal or carbon. In some preferred embodiments, in the film consists essentially of (e.g., consists of) redox-active, electrically conductive polymer and optionally a dopant capable of enhancing the electrical conductivity (and/or chemical stability) of the polymer. For instance, in a preferred embodiment the film consists essentially of, or consists of, PANI and phytic acid.

Receptor

The receptor is capable of binding to the target species.

The receptor is associated with the film. There is no particular limitation in the means for associating the receptor with the film, beyond that: (a) it is capable of remaining associated with the film when the electrode is in contact with the carrier medium (e.g., it is substantially not susceptible to becoming detached from the film and entering into the carrier medium); and (b) it is physically accessible to, and therefore capable of binding to, the target species when in contact with the carrier medium containing target species.

Methods for attaching receptors to polymers are well known in the art and substantially any such method can be used in order to associate the receptor with the film. For instance, those skilled in the art would be familiar with well-known techniques for associating antibodies and/or aptamers to the surface of solid substrate materials, including to polymer films. Typically such methods could involve carrying out chemical reactions between suitable corresponding functional groups on the receptor and polymer, respectively. For instance, one non-limiting well-known technique for associating an amine-containing polymer film (e.g. a PANI film) to amine-containing receptors (e.g. proteins such as antibodies) comprises activating the polymer film with glutaraldehye and attaching the receptors to the resulting, activated film.

Preferably, the receptor is capable of specifically binding to the target species. "Capable of specifically binding to the target species" typically means having a binding constant to the target species at least 50 times greater than the binding constant to any other substance(s) present in the carrier medium, preferably at least 100 times greater and more preferably still at least 200 times greater.

Examples of suitable receptors include antibodies, antibody fragments, nucleic acids, aptamers, oligosaccharides, peptides and proteins. Preferably, the receptor is selected from aptamers, antibodies, nucleic acids and peptides. More preferably the receptor is an aptamer or antibody, and most preferably an aptamer.

The antibody or the antibody fragment may be selected from one or more of the classes IgA, IgD, IgE, IgG and IgM. In a preferred embodiment, the antibody or antibody fragment is of the IgG type. The antibody binds selectively to the target species. The antibody or antibody fragment may be derived from a mammal, including, but not limited to, a mammal selected from a human, a mouse, a rat, a rabbit, a goat, a sheep, donkey and a horse. The aptamer may be selected from a peptide aptamer, a DNA aptamer and a RNA aptamer.

Clearly, the choice of receptor for a given electrode is determined by the identity of the target species. For a particular target species, a corresponding receptor that is capable of binding (preferably specifically binding) to the target species should be selected. As one illustrative example, if the target species is dengue NS1 protein (significant blood concentrations of which are associated with dengue virus infection), then the receptor should be a substance capable of binding (preferably specifically binding) to dengue NS1 protein, such as a dengue NS1 antibody.

In a preferred embodiment, the molecular weights (measured, for instance, in kDa) of the receptor and the target species, respectively, are controlled so as to optimise the sensitivity of the electrode for detecting the target species. In particular, it has been found that the range of the field effect giving rise to the sensitivity of the electrode to the presence of a target species can be optimised by decreasing the magnitude of the receptor molecular weight relative to the target species molecular weight, i.e. by increasing the ratio of target species molecular weight to receptor molecular weight. Consequently, low molecular weight receptor species may be preferable for optimising sensitivity, such as for instance via use of aptamer receptors compared with antibody receptors. This effect may at least in part be attributable to a physically smaller, lower molecular weight receptor allowing more intimate access of bound target species to the redox active species and underlying electrode surface. The role of the relative sizes of the target and receptor species is discussed in more detail, for instance, in WO 2019/145706.

Thus, the preferred ratio of target species molecular weight to receptor molecular weight ($M_w^{target}/M_w^{receptor}$) may, for instance, be at least 0.5, more preferably at least 1.0, more preferably still at least 10 and particularly preferably at least 25. There is no particular limit on the upper limit of preferred ratio of target species molecular weight to receptor molecular weight, but a notional practical upper limit may for instance be of the order of not more than 1000, e.g. not more than 500 or not more than 200.

Another advantage that may be associated with the use of the present polymer films compared with redox active moiety-harbouring monolayers is that they may be capable of supporting a higher surface coverage of receptor species. For instance, in certain embodiments the coverage of receptor on the working electrode may be in the range of 100 to 10000 ng/cm$^2$, such as 250 to 5000 ng/cm$^2$ or 500 to 2000 ng/cm$^2$.

Redox Capacitance Spectroscopy Using the Electrode

The electrode is used in an electrochemical method of sensing a target species, which method comprises: (A) contacting a carrier medium that may comprise said target species with the electrode (functioning as the working electrode); and (B) determining, via electrochemical capacitance spectroscopy, whether the target species is present in the carrier medium. As described elsewhere herein, the applicant has found that particular, unexpected advantages arise when utilising the electrode as a working electrode specifically in conjunction with electrochemical capacitance spectroscopy methods (for instance, compared with the ferrocene-based electrode films described in a number of previous electrochemical capacitance spectroscopy studies).

In step (A) of the method of the present invention, a carrier medium that may comprise said target species is contacted with the electrode. The electrochemical response of the system is sensitive to the presence of the target species. More specifically, the redox capacitance properties of the electrode are altered (typically the capacitance resulting from the intrinsic redox activity of the polymer film is lowered) if the target species is present and therefore binds to the receptor(s) of the electrode; similarly, the conductance properties of the electrode are altered if the target species is present and therefore binds to the receptor(s) of the electrode. Thus, if the carrier medium does contain the target species then a particular experimental measurement will be obtained. On the other hand the measurement will be different if the carrier medium does not contain the target species. Similarly, changes in the measurement will occur as the concentration of the target species in the carrier medium changes. Conveniently, the changes as a function of target species concentration can be quantified by way of a series of control experiments performed using carrier medium containing known concentrations of target species, which enables preparation of a calibration curve showing the results as a function of concentration and which can therefore be applied to establish the concentration of target species in a test carrier medium from the electrochemical measurements made on that system.

The carrier medium is preferably in liquid form although gaseous media are also be possible. The carrier liquid (or gas) may be any liquid (or gas) in which the target species can be suspended or dissolved (or dispersed). In an embodiment, the carrier liquid comprises water. In an embodiment, the carrier liquid comprises a biological fluid. A biological fluid may be a fluid that has been obtained from a subject, which may be a human or an animal. In an embodiment, the carrier liquid comprises an undiluted biological fluid. An undiluted biological fluid in the present context is a biological fluid obtained from a subject, e.g. a human or animal, that has not been diluted with another liquid. The biological fluid may be selected from blood, urine, tears, saliva, sweat, and cerebrospinal fluid. Optionally, the carrier medium comprises a biological fluid obtained from a subject, e.g. a human or animal, and a diluent. The diluent may be added to the biological fluid after it has been obtained from the subject. The diluent may include a liquid medium, e.g. a liquid medium selected from water and an alcohol, e.g. an alcohol, e.g. ethanol. The carrier medium may further comprise a buffer. The buffer may comprise a phosphate.

The target species is a substance that may or may not be present in the carrier medium, optionally together with one or more other non-target species, and which the users wishes to detect/sense. Most typically the method is one for determining the concentration of said target species in said carrier medium.

As described elsewhere herein, the method of the present invention comprises a step of performing electrochemical capacitance spectroscopy (and/or determining conductance), which in the present invention reports on the redox capacitance (and/or conductance) of the working electrode and specifically that conferred by the film comprising the redox-active polymer. The use of redox-active polymer to provide "in-built" redox activity means that it is not necessary (and indeed may be undesirable) for the carrier medium to comprise a separate/added redox-active species. This contrasts with certain prior art sensing methods that are based on electrochemical impedance methodology, which rely on the presence of an externally added redox-active species in the carrier medium (e.g. a metal complex such as an iron complex) in order to generate the measurement signals. Thus, in a preferred embodiment of the present invention the carrier medium does not contain any externally added redox-active species, e.g. it does not contain any (e.g. externally added) species that is redox-active in the range of potentials applied to the working electrode when the method of the invention is performed. Such a method can also be described as a "label-free" method.

Although this method can be used to detect a range of target species, one particularly useful aspect is the detection of a species of diagnostic interest. The sensitive detection of biomarkers in physiological samples is of ever growing interest in diagnosis. The methods of the present invention can be used in order sensitively and selectively to sense (and determine the concentration) of specific biomarkers, specifically by providing an electrode substrate that is functionalised with receptor moieties that are capable of specifically binding to the biomarker of interest.

Examples of target species include those selected from the group consisting of CRP protein, insulin and a marker of one or more of neurodegeneration, cancer, myocardial infarction, diabetes and general trauma.

More generally, suitable target species for detection in accordance with the methods of the invention include proteins, polypeptides, antibodies, nanoparticles, drugs, toxins, harmful gases, hazardous chemicals, explosives, viral particles, cells, multi-cellular organisms, cytokines and chemokines, ganietocyte, organelles, lipids, nucleic acid sequences, oligosaccharides, chemical intermediates of metabolic pathways and macromolecules. In preferred embodiments, the target species comprises, consists essentially of, or consists of, a biological molecule, more suitably a biological macromolecule, most suitably a polypeptide. A biomarker is one example of a biological molecule of particular interest.

If the target species is or comprises a protein, the protein may be selected from, but is not limited to, native proteins, denatured proteins, protein fragments, and prokaryotically or eukaryotically expressed proteins. Protein may have its normal meaning in the art, and most preferably 'protein' refers to a polypeptide molecule. Such polypeptide may comprise modifications such as glycosylation; phosphorylation or other such modifications.

If the target species is an antibody, the antibody may be selected from one or more of the classes IgA, IgD, IgE, IgG and IgM.

If the target species is a nanoparticle, the nanoparticle can be selected from, but is not limited to, one or more of insulating, metallic or semiconducting nanoparticles.

If the target species is a drug, the drug may be selected from, but is not limited to, alcohol (e.g. ethanol), amphetamines, amyl nitrate, heroin, ketamine, anabolic steroids, LSD, solvents, cannabis, cocaine (such as cocaine hydrochloride or 'coke'), tobacco, tranquilisers, crack (i.e. cocaine free base), ecstasy and/or gammhydroxybutyrate (GHB). Alternatively, in some embodiments, the drug may be a medicinal substance.

The target species may be a candidate drug, e.g. a chemical or biological entity that may be tested or screened for a particular activity or property using the present invention.

If the target species is a toxin, the toxin may be selected from, but is not limited to, one or more toxins originating from animals, plants, or bacteria.

If the target species is a viral particle, the viral particle may be selected from, but is not limited to, one or more viral particles with and without a genome.

If the target species is a cell, the cell may be selected from, but is not limited to, one or more of pluripotent progenitor cells, human cells (e.g. B-cells, T-cells, mast cells, phagocytes, neutrophils, eosinophils, macrophages, endothelial cells), cancerous cells (e.g. those originating from liver, cervical bone, pancreatic, colorectal, prostate, epidermal, brain, breast, lung, testicular, renal, bladder cancers), unicellular organisms of non-human origin, algae, fungi, bacteria, plant cells, parasite eggs, plasmodia and mycoplasma.

If the target species is an organelle, the organelle may be selected from, but is not limited to, one or more of nucleus, mitochondria, Golgi apparatus, endoplasmic reticulum, lysosome, phagosome, intracellular membranes, extracellular membranes, cytoskeleton, nuclear membrane, chromatin, nuclear matrix and chloroplasts.

If the target species is a lipid, the lipid may be selected from, but is not limited to, one or more of signalling lipids, structural lipids, phospholipids, glycolipids and fatty acids.

If the target species is nucleic acid sequence, the nucleic acid sequence may be selected from, but is not limited to, one or more of DNA, cDNA, RNA, rRNA, mRNA, miRNA and tRNA.

If the target species is an oligosaccharide, the oligosaccharide may be selected from, but is not limited to, one or more of oligosaccharides of human, animal, plant, fungal or bacterial origin.

The target species may be any antigen or analyte that is indicative of a particular disease. The target may be selected from, for example, dengue NS1 protein, C-reactive protein (CRP protein), D-dimer, angiotensin I converting enzyme (peptidyl-dipeptidase A) 1; adiponectin; advanced glycosylation end product-specific receptor; alpha-2-HS-glycoprotein; angiogenin, ribonuclease, RNase A family, 5; apolipoprotein A-1; apolipoprotein B (including Ag(x) antigen); apolipoprotein E; BCL2-associated X protein; B-cell CLL/lymphoma 2; complement C3; chemokine (C-C motif) ligand 2; CD 14, soluble; CD 40, soluble; cdk5; pentraxin-related; cathepsin B; dipeptidyl peptidase IV; Epidermal growth factor; endoglin; Fas; fibrinogen; ferritin; growth hormone 1; alanine aminotransferase; hepatocyte growth factor; haptoglobin; heat shock 70 kDa protein 1 B; intercellular adhesion molecule 1; insulin-like growth factor 1 (somatomedin C); insulin-like growth factor 1 receptor; insulin-like growth factor binding protein 1; insulin-like growth factor binding protein 2; insulin-like growth factor-binding protein 3; interleukin 18; interleukin 2 receptor, alpha; interleukin 2 receptor, beta; interleukin 6 (interferon, beta 2); interleukin 6 receptor; interleukin 6 signal transducer (gp130, oncostatin M receptor); interleukin 8; activin A; leptin (obesity homolog, mouse); plasminogen activator, tissue; proopiomelanocortin (adrenocorticotropin/beta-lipotropin/alpha-melanocyte stimulating hormone/beta-melanocyte stimulating hormone/beta-endorphin); proinsulin; resistin; selectin e (endothelial adhesion molecule 1); selectin P (granule membrane protein 140 kDa, antigen CD62); serpin peptidase inhibitor, clade E (nexin, plasminogen activator inhibitor type 1), member 1; serum/glucocorticoid regulated kinase; sex hormone-binding globulin; transforming growth factor, beta 1 (Camurati-Engelmann disease); TIMP metallopeptidase inhibitor 2; tumor necrosis factor receptor superfamily, member 1 B; vascular cell adhesion molecule 1 (VCAM-1); vascular endothelial growth factor; Factor II, Factor V, Factor VIII, Factor IX, Factor XI, Factor XII, F/fibrin degradation products, thrombin-antithrombin III complex, fibrinogen, plasminogen, prothrombin, and von Willebrand factor and the like. Markers useful for diabetes include for example C-reactive protein; glucose; insulin; TRIG; GPT; HSPA1 B; IGFBP2; LEP; ADIPOQ; CCL2; ENG; HP; IL2RA; SCp; SHBG; and TIMP2. Currently preferred target species include a target species selected from the group consisting of CRP protein, D-dimer, insulin and a marker of one or more of neurodegeneration, cancer, myocardial infarction, diabetes and general trauma. Another exemplary target species is dengue NS1 protein.

The target species may, for instance, comprise or consist of alpha-synuclein ($\alpha$-sync).

The target species may be a target associated with monitoring diabetes. In an embodiment, the target may be selected from glucose, insulin, Interleukin 2 receptor alpha (IL2-RA), C-reactive protein (CRP) and glycated hemoglobin (HbAlc). If the target species is glucose, the receptor moieties may be selected from, for example, the molecular recognition element of GDH-FAD assay or a glucose/galactose binding protein ("GGBP") (Scholle, et al., Mol. Gen. Genet 208:247-253 (1987)). If the target is IL-2RA, the receptor moieties may comprise or consist of a monoclonal antibody specific for IL-2RA. If the target species is or comprises C-reactive protein, preferably this is human C-reactive protein. If the target species is or comprises C-reactive protein, the receptor moieties may comprise or consist of anti-CRP. If the target species is or comprises insulin, the receptor moieties may comprise of consist of an insulin antibody.

Examples of specific target species currently of particular interest include an antigen or analyte selected from the group consisting of angiotensin I converting enzyme (peptidyl-dipeptidase A); adiponectin; advanced glycosylation end product-specific receptor; alpha-2-HS-glycoprotein; angiogenin, ribonuclease, RNase A family, 5; apolipoprotein A-1; apolipoprotein B (including Ag(x) antigen); apolipoprotein E; BCL2-associated X protein; B-cell CLL/lymphoma 2; complement C3; chemokine (C-C motif) ligand 2; CD 14, soluble; CD 40, soluble; cdk5; pentraxin-related; cathepsin B; dipeptidyl peptidase IV; Epidermal growth factor; endoglin; Fas; fibrinogen; ferritin; growth hormone 1; alanine aminotransferase; hepatocyte growth factor; haptoglobin; heat shock 70 kDa protein 1 B; intercellular adhesion molecule 1; insulin-like growth factor 1 (somatomedin C); insulin-like growth factor 1 receptor; insulin-like growth factor binding protein 1; insulin-like growth factor binding protein 2; insulin-like growth factor-binding protein 3; interleukin 18; interleukin 2 receptor, alpha; interleukin 2 receptor, beta; interleukin 6 (interferon, beta 2); interleukin 6 receptor; interleukin 6 signal transducer (gp130, oncostatin M receptor); interleukin 8; activin A; leptin (obesity homolog, mouse); plasminogen activator, tissue; proopiomelanocortin (adrenocorticotropin/beta-lipotropin/alphamelanocyte stimulating hormone/beta-melanocyte stimulating hormone/beta-endorphin); proinsulin; resistin; selectin e (endothelial adhesion molecule 1); selectin P (granule membrane protein 140 kDa, antigen CD62); serpin peptidase inhibitor, Glade E (nexin, plasminogen activator inhibitor type 1), member 1; serum/glucocorticoid regulated kinase; sex hormone-binding globulin; transforming growth factor, beta 1 (Camurati-Engelmann disease); TIMP metallopeptidase inhibitor 2; tumor necrosis factor receptor superfamily, member 1 B; vascular cell adhesion molecule 1 (VCAM-1); vascular endothelial growth factor; Factor II, Factor V, Factor VIII, Factor IX, Factor XI, Factor XII, F/fibrin degradation products, thrombin-antithrombin III complex, fibrinogen, plasminogen, prothrombin, and von Willebrand factor and the like. Markers useful for diabetes include for example C-reactive protein; glucose; insulin; TRIG; GPT; HSPA1 B; IGFBP2; LEP; ADIPOQ; CCL2; ENG; HP; IL2RA; SCp; SHBG; and TIMP2.

Step (B) of the method of the present invention frequently comprises determining, via electrochemical capacitance spectroscopy, whether the target species is present in the carrier medium.

Electrochemical capacitance spectroscopy refers at its most general to a spectroscopic method which comprises interrogating (by electrochemical means) the redox capacitance, $C_r$, and/or related measurement parameters such as C' and/or C", of the electrode defined herein. In electrochemical capacitance spectroscopy, the electrode possesses an intrinsic redox capacitance as a result of the presence of the redox active, conducting polymer film. The redox capacitance of the electrode is modified if a target species binds to the receptor that is also comprised by the electrode.

Redox capacitance spectroscopy is known in the art and the present document does not seek to be a primer on its scope or specific application. In general, the method of the invention encompasses any method that involves interrogating the redox capacitance of the electrode in order to determine whether the electrode comprises a bound target species. Representative examples of disclosure relating to application of redox capacitance spectroscopy for detecting target species (but using different redox-active species on the working electrode, such as ferrocene moieties attached to self-assembled monolayers) can be found in WO 2015/022483, WO 2016/120606, J. Phys. Chem. B 2012, 116, 30, 8822-8829, Biosensors and Bioelectronics 50 (2013) 437-440, Biosensors and Bioelectronics 57 (2014) 96-102 and WO 2019/145706, the contents of all of which are herein incorporated by reference in their entirety. Further guidance on exemplary, but non-limiting, specific redox capacitance spectroscopic principles can found in the working Examples of this disclosure.

For ease of understanding one exemplary redox capacitance spectroscopy method, as previously disclosed in WO 2016/120606, is described in more detail below.

Generally, a varying ac potential is applied on a bias (or DC) potential between a working electrode and a counter electrode. Scanning is conducted across a range of ac frequencies $\omega$. The ratio of the input signal (typically the varying potential) to the output signal (typically the varying current) allows the impedance to be calculated. There is generally a phase difference between the input signal and the output signal, such that the impedance can be considered as a complex function Z*, having a real part (sometimes termed Z') and an imaginary part (sometimes termed Z").

The frequency range of the varying ac potential applied may be from 1 mHz to 10 MHz. The amplitude of the applied ac potential, which is typically in the form of a sine wave, may be from 1 mV to 100 mV, optionally from 5 mV to 50 mV, optionally from 5 mV to 20 mV, optionally from 5 mV to 15 mV, optionally 8 mV to 12 mV, optionally about 10 mV.

When conducting a measurement, the bias potential (or direct current potential) may be set at any desired value. This DC or bias potential is known herein as the applied potential. An exemplary method of the present invention involves obtaining a plurality of measurements of the complex impedance across a range of applied potentials (which allows for the subsequent integration over applied voltage), i.e. a number of EIS measurements are obtained each at different selected voltages. Typically the plurality of measurements of the complex impedance obtained is at least three measurements, preferably at least five measurements, such as at least ten or even at least twenty measurements, i.e. the range of applied potentials typically comprises at least three different applied potentials, preferably at least five different applied potentials, such as at least ten or even at least twenty different applied potentials.

In the step of converting the plurality of measurements of Z* into a plurality of measurements of the real component of the complex capacitance, C', measurements of C' at a (fixed/single) selected frequency $\omega$ are used. As would be well known to a skilled person C' typically varies as $\omega$ changes (i.e. C' is a function of $\omega$). The appropriate selected frequency $\omega$ will of course depend on the construction of a particular electrode and on the nature of the sensing method being undertaken. However, determination of a suitable selected frequency $\omega$ is routine. The skilled person could easily, for example, identify a value of $\omega$ where the obtained values of C' are satisfactorily high (e.g. at or close to the maximum value of C' across the frequency range applied in a routine electrochemical impedance spectroscopic scan). Analogous principles apply when the plurality of measurements of Z* are converted into a plurality of measurements of the imaginary component of the complex capacitance, C".

Conversion of Z* at the selected frequency $\omega$ into C' and/or C" is routine and well known in the art. In particular, in a standard analysis, the complex impedance function Z*($\omega$) at a particular potential can be converted phasorially into complex capacitance C*($\omega$) with its real and imaginary components, using the equation $C^*(\omega)=1/i\omega Z^*(\omega)$.

Integration of the measurements of C' and/or C" as a function of applied voltage can also be routinely performed, for example using "area under the graph methods" when C', C" or any combination of C' and C" is plotted against applied voltage and/or by way of well-known and routine computerised algorithms for integrating empirically derived data.

Integration of either C' and C" at the selected frequency $\omega$ as a function of applied voltage provides an "integrated measurement value" that is suitable for sensing. Specifically, an integrated measurement value derived from the integration of C' is related to the density of states (DOS) of the system, i.e. it reflects the quantum capacitance. An integrated measurement value derived from the integration of C" is related to the conductance of the system.

In practice, it may sometimes be preferable (for pure simplicity of operation) to obtain the integrated measurement value by integration of only one of C' and C" at the selected frequency $\omega$ as a function of applied voltage. In a first preferred embodiment, therefore, the plurality of measurements of Z* is converted into a plurality of measurements of the real component of the complex capacitance, C' at the selected frequency ω and these measurements are converted as a function of applied voltage to obtain the integrated measurement value. Further, in a second preferred embodiment, the plurality of measurements of Z* is converted into a plurality of measurements of the imaginary component of the complex capacitance, C" at the selected frequency ω and these measurements are converted as a function of applied voltage to obtain the integrated measurement value.

However, since both C' and C" can be used, it will also be apparent to the skilled person that an integrated measurement value can be obtained by integrating any combination of C' and C", at the selected frequency co as a function of applied voltage. For example, any sum of the values of C' and C" (where C' and/or C" are possibly weighted with any negative or positive constants) or any multiple or quotient of the values of C' and C" can be used.

The integrated measurement value is typically compared with one or more reference values. The reference value(s) can be obtained by obtaining one or more corresponding integrated measurement values under conditions where the concentration of the target species is already known. In other words, the reference value(s) are used to calibrate the integrated measurement value obtained when the method is performed under test conditions with expected values that would be obtained under specific, known conditions. Calibration of an apparatus for use in sensing applications is well known and routine in the art.

Figure 4:
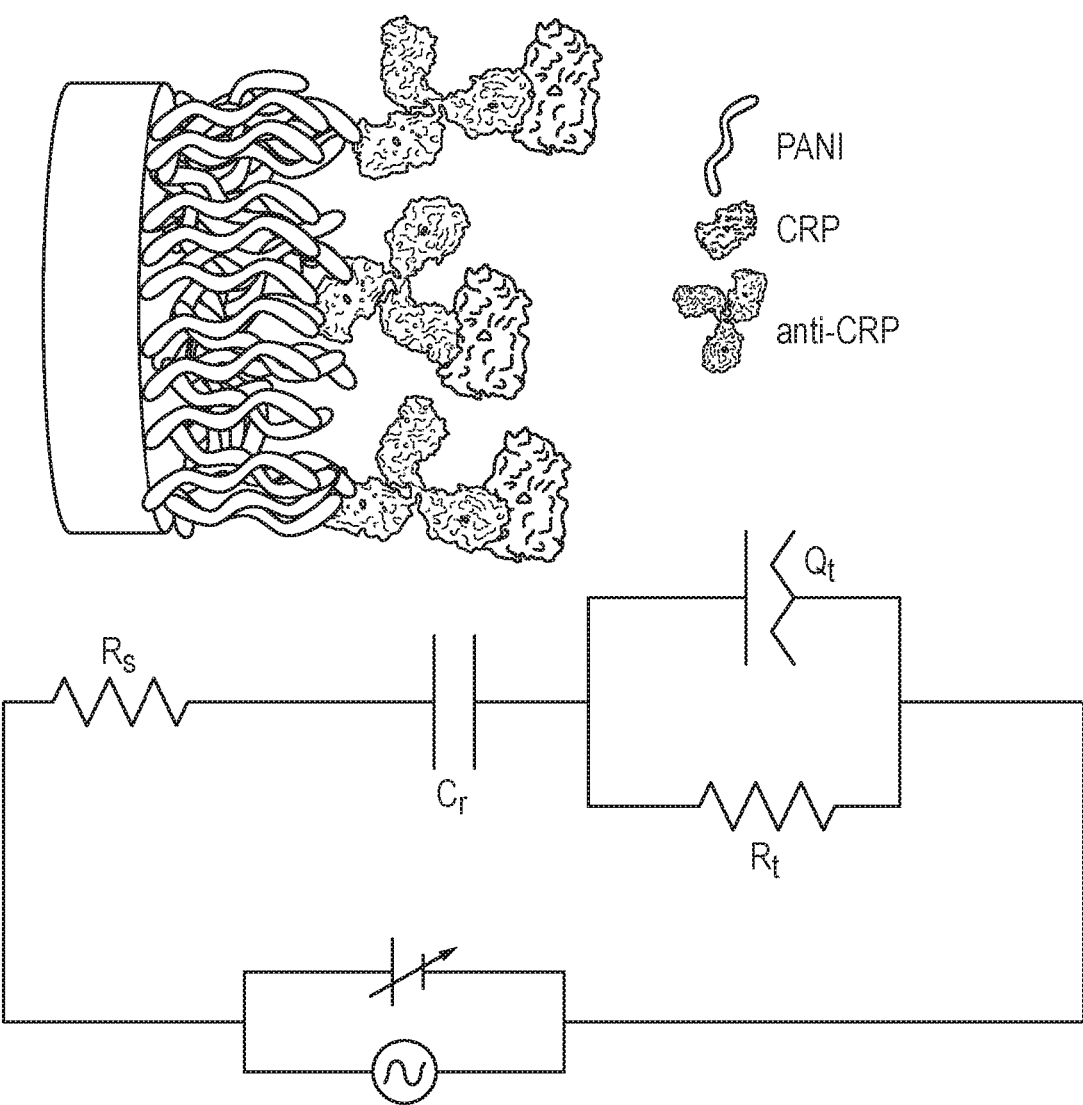
FIG. 4 provides a schematic depiction of a PANI-modified screen printed carbon electrode including anti-CRP receptors, as detailed in Example 1. The bottom section of the Figure shows an equivalent circuit diagram for data fitting of the capacitive data, where $R_s$=solution resistance, $C_r$=redox capacitance and $Q_t$ and $R_t$ are additional constant phase and capacitive elements that describe non-ideal features associated with the porous polymer (in Example 1 only the Cr element is considered).

Returning more generally to the principles of redox capacitance spectroscopy, it is also possible to perform the method of the invention by other means, provided that this involves measurement of the redox capacitance of the system (or the related principle of its conductance, as further discussed elsewhere herein). For instance, it is also possible to perform the methods of the invention by measuring the redox-capacitance ($C_r$) of the electrode in the presence of the carrier medium (as demonstrated in Example 1 below). Briefly, the redox-capacitance ($C_r$) can, for instance, be resolved at, or near, the half-wave potential (and, most generally, anywhere within the redox active window), graphically as the semi-circle diameter in a capacitive Nyquist plot (e.g. at around –0.16 V for a polymer film comprising PANI—such as at any potential in the range from –0.4 V to 0.4 V, more preferably –0.1 to –0.2 V). Alternatively, this capacitance can also be obtained by fitting to an equivalent circuit (FIG. 4), where $R_s$ is the solution resistance and $C_r$ the redox capacitance. $Q_t$ and $R_t$ are additional parameters that account for the non-ideal behaviour of the porous polymer (for further details, see, e.g.: Li et al. Anal. Chem. 2012, 84 (8), 3485-3488; Peng et al. ACS Energy Lett. 2018, 3 (7), 1477-1481; and Fournier-Wirth et al. Anal. Chem. 2007, 79 (13), 4879-4886; optionally these parameters can be omitted in an approximate (empirical) model). Still further, it is possible to obtain measurements of the redox capacitance, $C_r$, by any other electrochemical means, including for instance square-wave voltammetry (SWV) (again, Example 1 demonstrates how SWV can be applied to obtain such measurements). All of these techniques are well known methods in the art for obtaining measurements of the redox-capacitance ($C_r$) of a working electrode in a carrier medium, which would be familiar to those skilled in the art and could readily be applied to determining the redox capacitance in accordance with the methods of the present invention.

In a further embodiment of the present invention, the electrochemical capacitance spectroscopy is used to interrogate the conductance of the electrode comprising the film, receptor and, possibly, the bound target species. A specific exemplary (but non-limiting) such method is outlined in Example 2 of the present application. The redox capacitance ($C_r$) is mathematically related to the conductance (G) as described elsewhere herein. By performing electrochemical impedance spectroscopy on a system comprising the electrode and a carrier medium that may comprise the target species, directly measured electrochemical properties can be converted into a measurement of the conductance, G, whereupon the conductance is used to determine whether the target species is present in the carrier medium (see, e.g., Example 2). For example, the measured conductance can be used to determine the concentration of the target species. Determining the presence, or the concentration, of the target species can be done by comparing the measured conductance with reference values (e.g. obtained by calibrating the system using known concentrations of target species), as would be readily appreciated by those skilled in the art, and by analogy to the principles described elsewhere herein.

As such, the method of the present invention can involve, in step (B), determining, via electrochemical capacitance spectroscopy that comprises determining the conductance of the electrode, whether the target species is present in the carrier medium. Alternatively, and in view of the relationship between the capacitance and conductance of the electrode, the method of the invention, in this embodiment, can alternatively be characterised as being one in which step (B) is determining, via electrochemically determining the conductance of the electrode, whether the target species is present in the carrier medium. For the avoidance of doubt, in this embodiment of the method exactly the same preferred, optional features (e.g., relating to the composition and structure of electrode components, target species, carrier media, etc.) apply as disclosed elsewhere throughout this application in relation to the electrochemical method of sensing a target species.

When carrying out the method of the invention it has been found that advantageous limits of detection ("LOD") can be achieved. For instance, in preferred embodiments the limit of detection of the target analyte may be lower than 5 μg/mL, preferably lower than 2.5 μg/mL and more preferably still lower than 1 μg/mL (e.g. approximately 0.5 μg/mL or lower). For a particular embodiment (target analyte identity, working electrode construction, etc.) LOD can be determined, for instance, according to LOD=3σ/s, where s is the slope of the linear region of the calibration curve for concentration of the target species as a function of redox capacitance measured and σ the standard deviation of the blank.

It has also been found that the methods of the invention can achieve beneficially high sensitivity (i.e., distinguishable changes in measured response as a function of only small changes in target species concentration). While high sensitivity can be achieved for all aspects of the method of the invention, particularly high sensitivity may be possible when the methods involve determining the conductance of the electrode (compare, for instance the sensitivity achieved in the system exemplified in Example 2 as compared with that in Example 1).

Apparatus

The methods of the present invention can be conducted on a suitable apparatus. This apparatus comprises an electrochemical spectrometer comprising the working electrode as described herein. The spectrometer typically further comprises a reference electrode and/or a counter electrode.

The apparatus optionally further comprises (a) a receiver configured to receive, from said electrochemical spectrometer, input data comprising redox capacitance measurements made on the electrode; and (b) a processor configured to convert said measurements into output data concerning the presence of absence of the target species in the carrier medium (e.g., the concentration of the target species). The receiver and processor can be part of a computer. The functionality of the receiver and processor can be achieved by programming the computer to receive input data from the method of the invention and to process these data into the output data as described herein.

EXAMPLES

Example 1

Electrochemical Experiments

All electrochemical experiments were carried out with a PalmSens potentiostat in a three-electrode configuration comprising a screen-printed graphene nanoplate working electrode (SPE), a screen printed Ag reference electrode and a screen printed Au counter electrode. All potentials are reported with respect to the Ag reference electrode. All experiments were carried out in 0.1 M phosphate buffer ("PB"), pH=7.4, unless otherwise stated. Cyclic voltammetry (CV) was carried out at a scan rate of 100 mV/s. Square-wave voltammograms (SWV) were measured with a step potential of 5 mV, an amplitude of 50 mV and a frequency of 10 Hz. Electrochemical impedance spectroscopy was performed between 9 kHz to 0.1 Hz (20 frequencies), with a sigmoidal AC perturbation of 10 mV (peak-to-peak). These experiments were carried out at different DC potentials including the "redox-in" potential (OCP; −0.16 V, the half-wave potential of PANI-film), the "redox-out" potential (0.4 V, no redox-activity) as well as between −0.8-0.4 V (20 mV potential steps) at a fixed frequency of 0.1 Hz with waiting time of 5 s. Impedance-derived capacitance was obtained via $C''(\omega)=Z'/\omega Z^2$ and $C'(\omega)=Z''/\omega Z^2$, where $\omega$ is the angular frequency. The capacitance of the interface was obtained either graphically as the diameter of the semicircular region in the capacitive Nyquist plots or via circuit fitting as discussed in more detail below. Circuit fitting and data analysis was carried out with PSTrace software 5.7. The relative response (RR %), i.e. the decrease in $C_r$, was normalised as follows:

$$RR\ \% = -\frac{C_r - C_{r0}}{C_r} \times 100\%.$$

Langmuir-Freundlich isotherms were fitted according to $$\theta = \frac{K \times [CRP]^n}{1 + K \times [CRP]^n}.$$

The limit of detection (LOD) was determined according to LOD=3σ/s, where s is the slope of the linear region of the calibration curve and σ the standard deviation of the blank.

Sensor Construction

The electrodes were washed with copious amounts of water followed by electrochemical polishing in 0.1 M KOH, between −1.0 to 1.3 V for 20 cycles. The electroactive surface area of the cleaned electrodes was determined via the Randles-Sevcik equation by measuring the CV of the $Fe(CN)_6^{3-/4-}$ couple (5 mM in 0.1 M PB), utilising a diffusion coefficient of $7.60\times10^{-6}$ $cm^2$/s. This afforded an electroactive surface area of 0.0056 $cm^2$, 1.47 times larger than the geometrical area. Electropolymerisation was carried out in an aqueous solution of 1 mL 98% aniline and 2 mL of 50% phytic acid in 17 mL of MilliQ water by applying a current density of 10 μA/$cm^2$ for 5, 10, 20, 40 or 80 min. The films were rinsed with and then equilibrated in 0.1 M PB for 10 min before further characterisation. Covalent immobilization of the receptor was carried out by exposure of the PANI-PA films to 2.5% glutaraldehyde (in PB) for 30 min, followed by rinsing with copious amounts of PB. The antibodies were then coupled to the activated interface by exposure to 5 μg/mL anti-CRP or 5 μg/mL anti-D-dimer for 30 min. After rinsing with 0.1 M 7.4 pH PB remaining active sites were deactivated with 10 mM ethanolamine in 0.1 M 7.4 pH PB for 30 min followed by rinsing with PB.

Protein Assays

The sensor was equilibrated in PB for 30 min to obtain a stable baseline. Afterwards the sensor was exposed to increasing CRP concentration (0.25, 0.5, 1, 2, 4, 8, 16 μg/mL)) for 10 minutes followed by rinsing with copious amounts of PB. The redox capacitance was then measured in pure PB as described above.

Results and Discussion

Figure 2A:
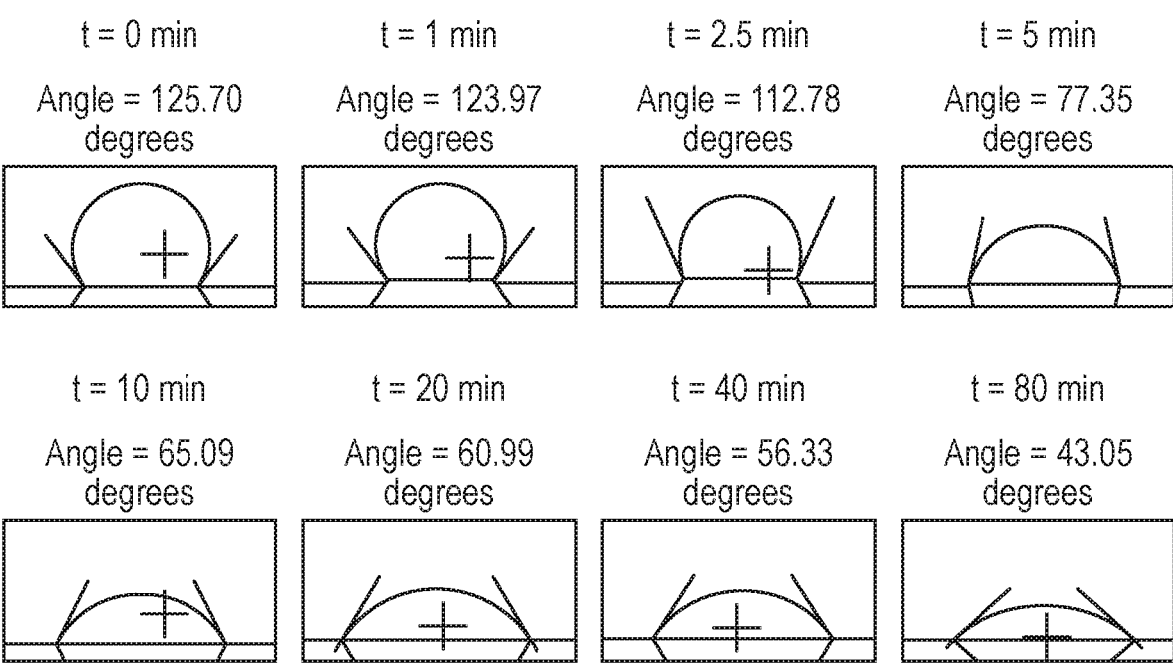
FIG. 2 shows static water contact angles on PANI-modified electrodes after different polymerization times, as described in Example 1: panel a) shows representative pictures of contact angle measurement; panel b) shows water contact angles as function of polymerisation time.
Figure 2B:
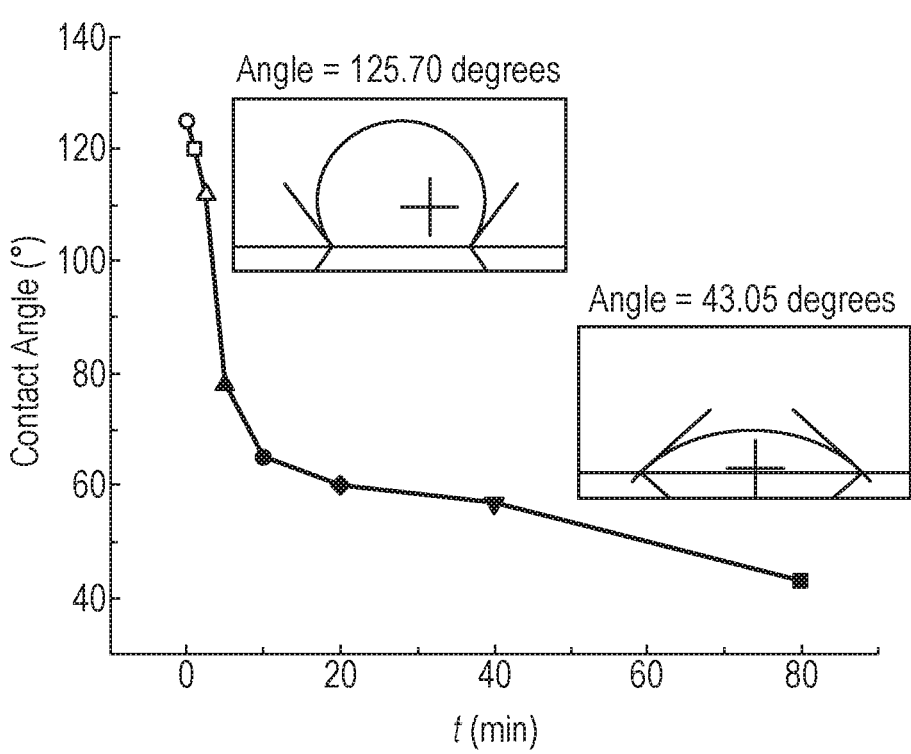

Phytic acid-doped polyaniline (PANI-PA) films on screen printed graphene nanoplate electrodes were generated by applying a controlled current density for specific and varied amounts of time (between 5-80 min, as discussed above). The FT-ATR-IR signatures of the so-generated films include peaks at 1097, 1248 and 1719 $cm^{-1}$ (FIG. 1). The latter most likely arises from the phosphate groups of the phytic acid, indicating incorporation into the polymeric film. Phytic acid doping has been previously shown to endow the PANI films with higher conductivity in physiological pH and high hydrophilicity. The latter is commonly associated with an increased resistance to non-specific adsorption and was assessed here by water contact angle measurements. As can be seen in FIG. 2 the high water contact angle of the bare electrode (126°) is indicative of a hydrophobic interface which becomes gradually more hydrophilic with increasing PANI deposition (polymerization time). After 80 min a relatively hydrophilic film (43°) can be obtained.

Figure 3A:
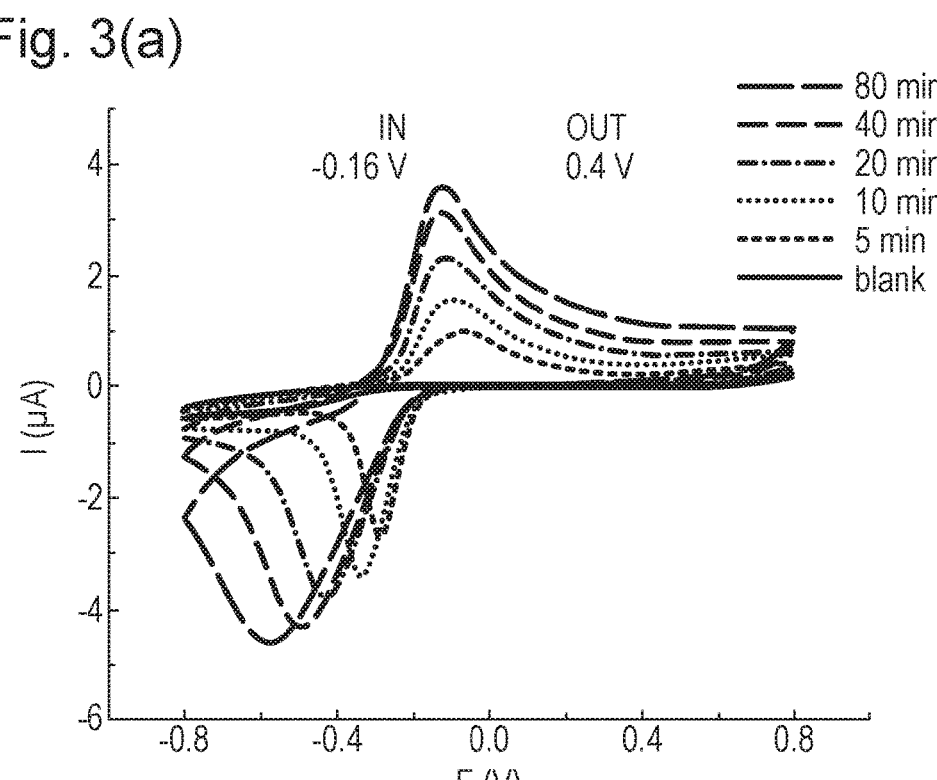
FIG. 3 shows electrochemical characterisation of phytic acid-doped PANI films after different polymerization times (5-80 min) in 0.1 M PB, pH 7.4, as described in Example 1: panel a) shows CVs at a scan rate of $100 \text{ mVs}^{-1}$—traces are shown for each of films polymerised for 80 min, 40 min, 20 min, 10 min, 5 min and with no film, with the 80 min trace being that with the largest peak in maximum and minimum I and with progressively lower peaks in maximum and minimum I being exhibited for films polymerised for lower times; panel b) shows capacitive Nyquist plots at redox IN potential (−0.16 V) where $C_r$ can be resolved as the diameter of the semicircular region; panel b) inset shows the temporal stability of $C_r$—after an initial signal decrease the baseline is stable within ≤2%.
Figure 3B:
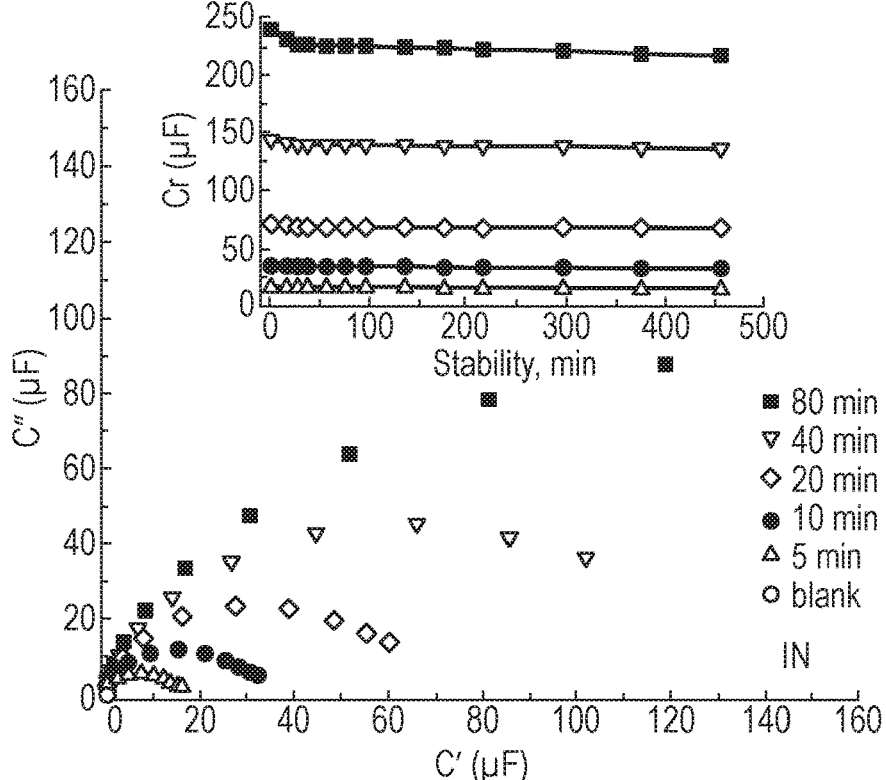
Figure 5:
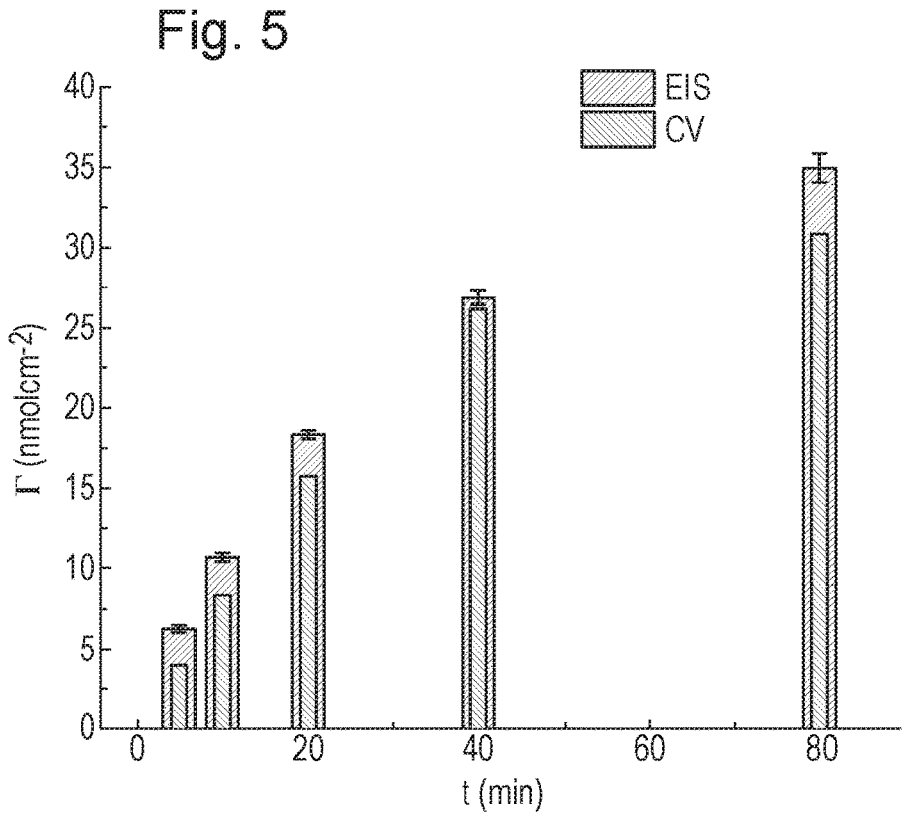
FIG. 5 provides a comparison of molecular surface coverage (Γ) calculated from CV and EIS methodologies (bars representing the former are enclosed within the bars representing the latter). Error bars represent one standard deviation from 12 measurements.

The electrogenerated PANI-PA films were investigated by CV and EIS in 0.1 M PB, pH=7.4 in the absence of any solution-phase redox probe. As can be seen in FIG. 3, panel a), and FIG. 2, the PANI films display a well-defined quasi-reversible redox couple at −0.16 V whose peak currents are, as expected, proportional to polymerization time (5-80 min). This is indicative of a continuous growth of the PANI film even at long polymerization times and enables good control over the PANI surface coverage and thus thickness. An increased film thickness also induces a larger peak separation, indicative of a predictably and progressively reduced electron transfer rate through thicker films. These general observations were also confirmed by impedance-derived capacitance measurements. In the capacitive Nyquist plots (FIG. 3, panel b)) an increased redox-capacitance ($C_r$) at the "redox-in" potential (i.e. half-wave potential) can be resolved as the semi-circle diameter, which, again, is proportional to the polymerization time. This capacitance can also be obtained by fitting to an equivalent circuit (FIG. 4), where $R_s$ is the solution resistance and $C_r$ the redox capacitance. $Q_t$ and $R_t$ are additional parameters that account for the non-ideal behaviour of the porous polymer (for further details, see, e.g.: Li et al. Anal. Chem. 2012, 84 (8), 3485-3488; Peng et al. ACS Energy Lett. 2018, 3 (7), 1477-1481; and Fournier-Wirth et al. Anal. Chem. 2007, 79 (13), 4879-4886). Importantly, $C_r$ obtained via circuit fitting (utilized throughout herein) is almost identical to that obtained by graphical analysis and can further be utilized to quantify the surface coverage ($\Gamma$) of redox active aniline subunits (for further details see Bueno et al. Anal. Chem. 2014, 86 (3), 1337-1341). The hereby obtained molecular surface coverage (6-35 nmolcm$^{-2}$) is in a good agreement with that obtained by integration of the peak area in the CVs (deviations 2-20%, FIG. 5, Table 1).

TABLE 1

Molecular surface coverages of redox-active PANI units as determined by CV and EIS.

| Polymerisation time, min | Molecular coverage, $\Gamma$, nmolcm$^{-2}$ | |
|---|---|---|
| | CV | EIS (Cr from fitted Nyquist) |
| 5 | 4.01 ± 0.20 | 6.14 ± 0.22 |
| 10 | 8.40 ± 0.41 | 10.64 ± 0.26 |
| 20 | 15.73 ± 0.59 | 18.30 ± 0.27 |
| 40 | 26.21 ± 0.65 | 26.78 ± 0.41 |
| 80 | 30.84 ± 1.66 | 34.91 ± 0.91 |

Figure 6:
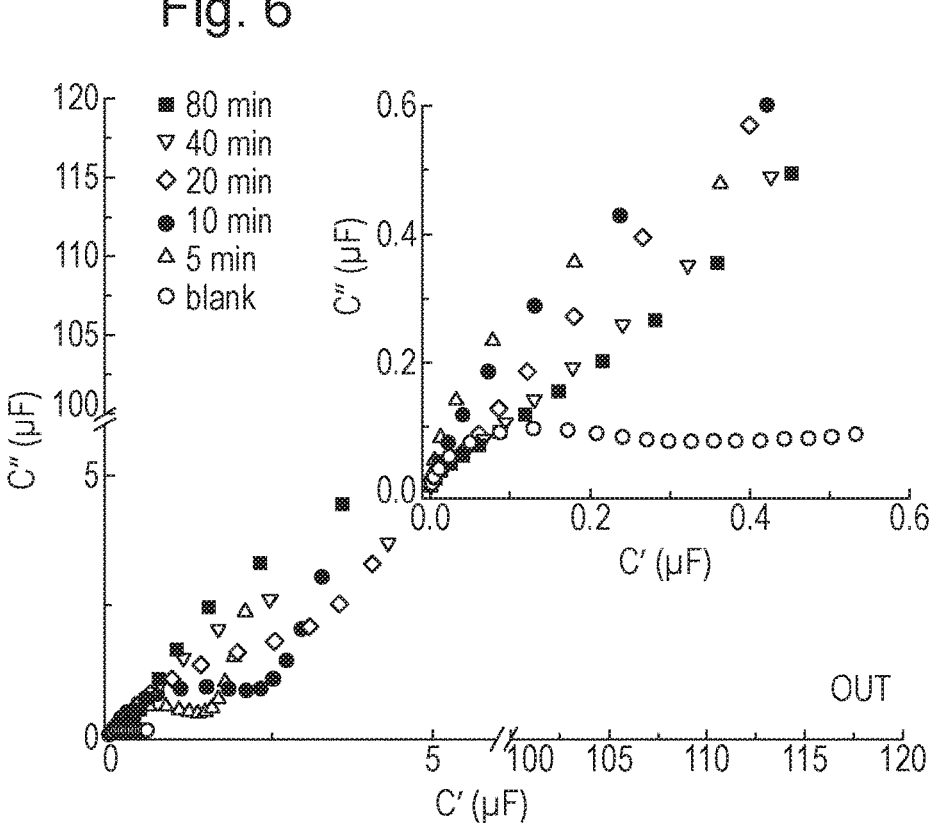
FIG. 6 shows capacitive Nyquist plots at redox "out" potential (0.4 V) at different polymerization times, as described in Example 1 (Inset: Enlarged plots at low capacitances, showing redox capacitance of the bare electrode).
Figure 7A:
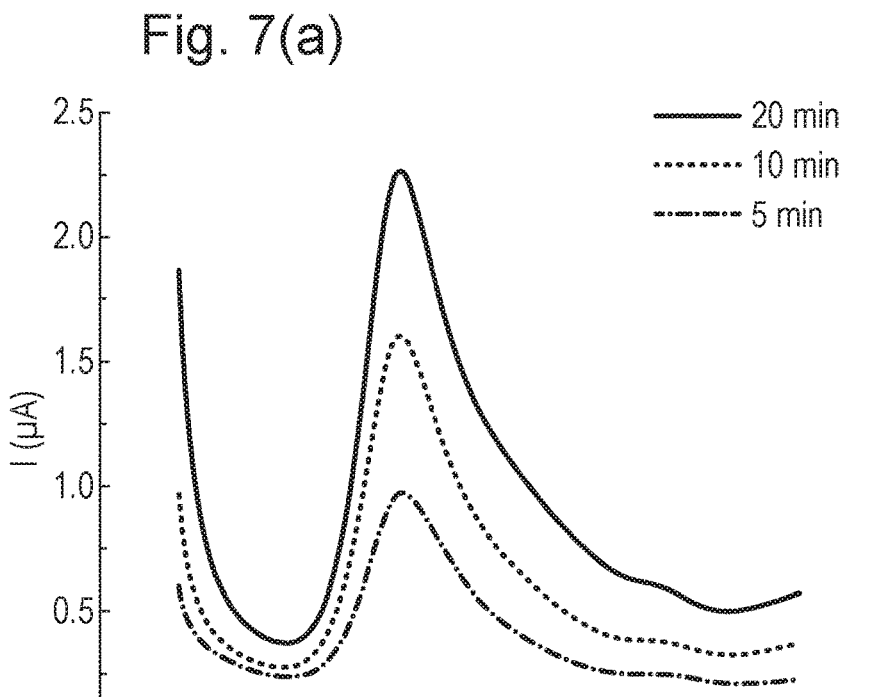
FIG. 7 shows: in panel a), SWV of PANI-PA films after different polymerization times (measured with a step potential of 5 mV, an amplitude of 50 mV and a frequency of 10 Hz) as described in Example—top trace (i.e., with highest peak) is film polymerised for 20 min, middle trace for 10 min and bottom trace for 5 min; and, in panel b), $C_r$ as approximated by C' at 0.1 Hz at different DC potentials (thicker polymer films are not shown because $C_r$ cannot be resolved at experimentally accessible frequencies).
Figure 7B:
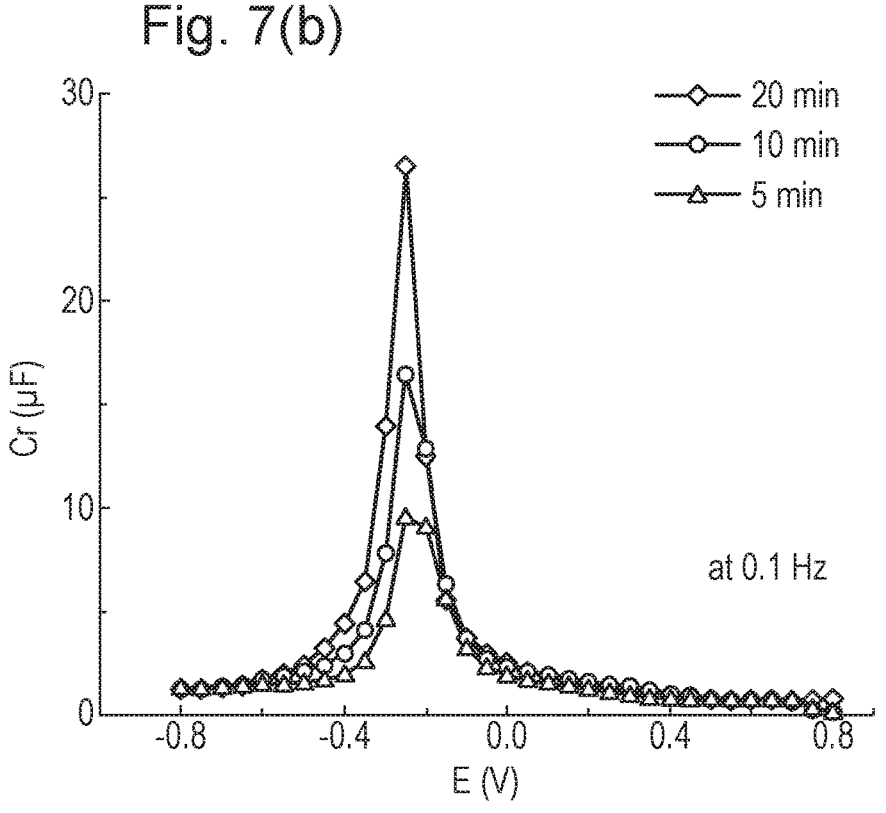

The same capacitive analyses outside of the window of PANI Faradaic activity (0.4 V), resolve capacitances that are much smaller (by at least one order of magnitude, FIG. 6) than $C_r$ measured at the redox potential. A direct analysis of capacitance at different potentials as described previously (for further details see Bueno et al. Anal. Chem. 2014, 86 (4), 1997-2004) confirms $C_r$ to be directly correlated with the Faradaic activity of the film as resolved by SWV (FIG. 7). Importantly, the baseline stability of $C_r$ is excellent for all PANI-PA films (see inset of FIG. 3, panel b)), being negligible after an initial brief stabilization.

Figure 8A:
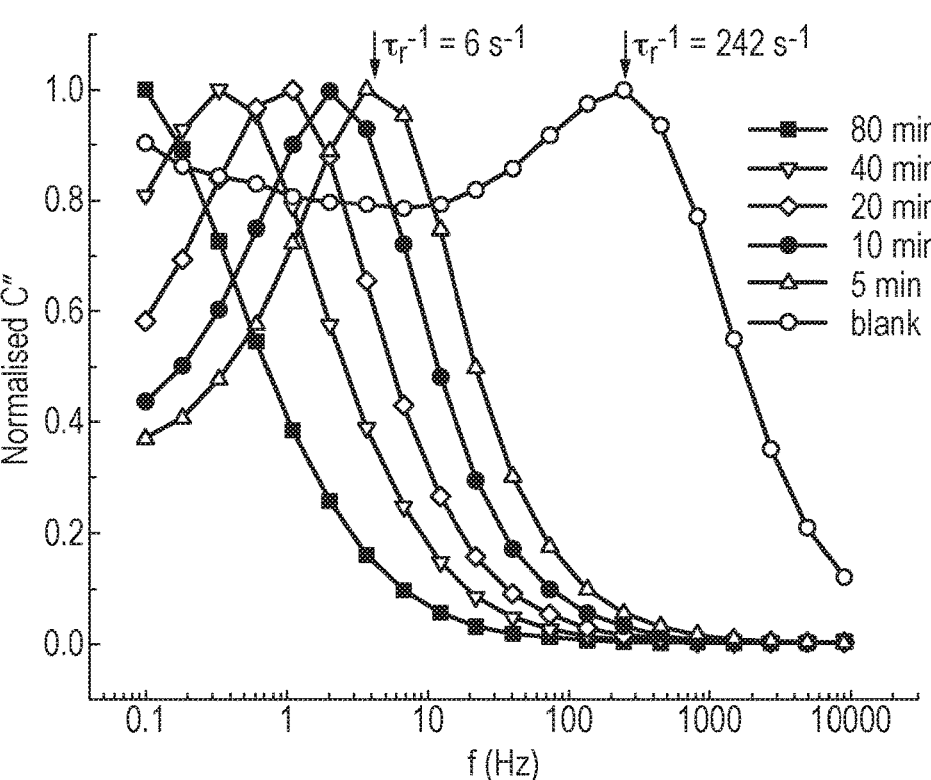
FIG. 8 shows electrochemical characterisation of PANI-PA films after different polymerization times in 0.1 M PB, 7.4 pH, as described in Example 1: panel a) shows a normalised Bode plot of C''; panel b) shows its associated relaxation time constant ($\tau_r$).
Figure 8B:
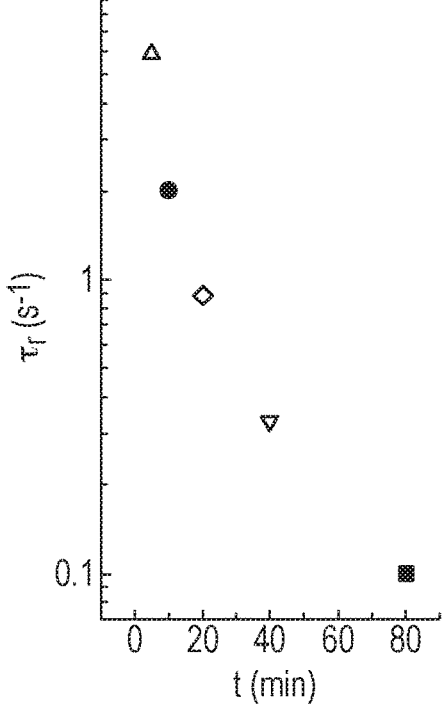

Further analysis of the EIS data showed that the relaxation time constant ($\tau_r$), which is associated with the Faradaic charging event, decreases with increasing film thickness (FIG. 8, Table 2), indicative of slower electron transfer as similarly resolved by CV (vide supra) (see Bueno et al. Anal. Chem. 2014, 86 (4), 1997-2004).

TABLE 2

$\tau_r$ of PANI films after different polymerization times at redox "in" potential

| Polymerisation time, min | $\tau_r$ (s$^{-1}$) | $1/\tau_r$ (s) |
|---|---|---|
| 0 | 242.12 | 0.0041 |
| 5 | 5.87 | 0.170 |
| 10 | 2.05 | 0.487 |
| 20 | 0.89 | 1.123 |
| 40 | 0.33 | 3.030 |
| 80 | 0.10 | 10.00 |

Subsequently, signal response/suppression of the PANI-PA films upon exposure to (several dilutions and 100%) fetal bovine serum (FBS) was studied, an analysis which indirectly reports on fouling. Across all serum concentrations utilized the relative response (relative decrease in capacitance) was largest for the thinnest PANI film (5 min polymerisation), with thicker films being associated with a reduced signal suppression/fouling (FIG. 9), an empirical observation in good agreement with enhanced interfacial hydration (as assessed by water contact angles). As expected, fouling is generally lower for more diluted FBS media.

The so-generated films, with their tuneable redox capacitance and fouling profile, can be instilled with selective recognition characteristics through the facile integration of receptors. As proof-of-concept, CRP, a clinically relevant biomarker for cardiovascular health, was chosen as the analyte and assayed in pure PB and 1% FBS. A selective CRP-receptive PANI-based interface was constructed by immobilization of anti-CRP via glutaraldehyde crosslinking of amine functionalities in the PANI film and the antibody. This induced a significant $C_r$ response (75% signal change, from 32.7±2.1 µF (PANI-10 min) to 8.15±0.32 µF (PANI/anti-CRP)) as shown in FIG. 10, consistent with a large degree of anti-CRP recruitment. This was further confirmed by assessing the anti-CRP depletion from the immobilization solution using the Bradford assay, which revealed a total anti-CRP coverage of 909±80 ng/cm$^2$ on PANI-10 min. This receptor coverage is, as expected, larger than a monolayer coverage, but interestingly also larger than that reported for other PANI films (see also Geddes et al. Thin Solid Films 1995, 260 (2), 192-199 and Sai et al. Anal. Chem. 2006, 78 (24), 8368-8373).

Figure 11A:
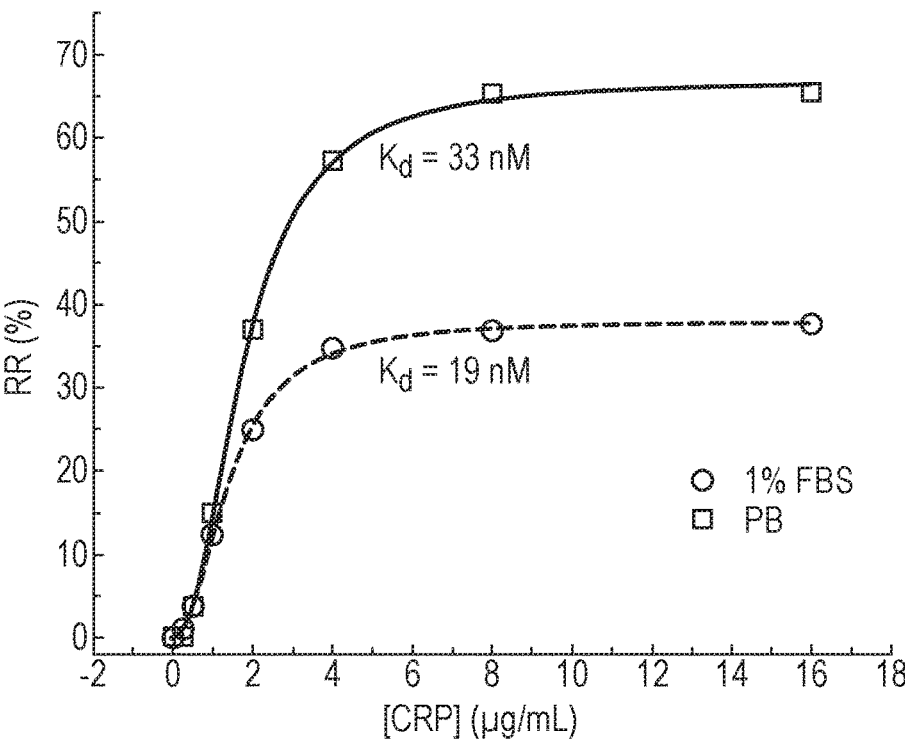
FIG. 11 shows, as described in Example 1: in panel a), relative response of PANI-10 min/anti-CRP towards CRP in PB and in 1% of FBS in clinically relevant range—the data was fitted to a Langmuir-Freundlich isotherm; and, in panel b), relative response of anti-CRP or anti-D-dimer-modified PANI-10min after exposure to 2 μg/mL of CRP or D-dimer in 1% FBS—error bars represent one standard deviation from independent measurements on different electrodes.
Figure 11B:
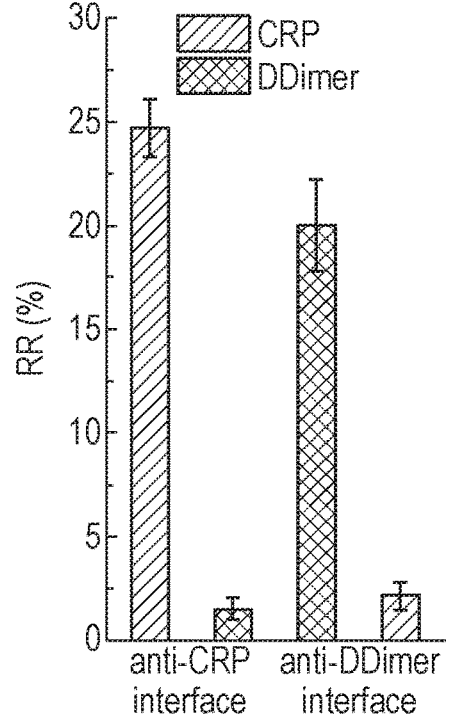
Figure 12A:
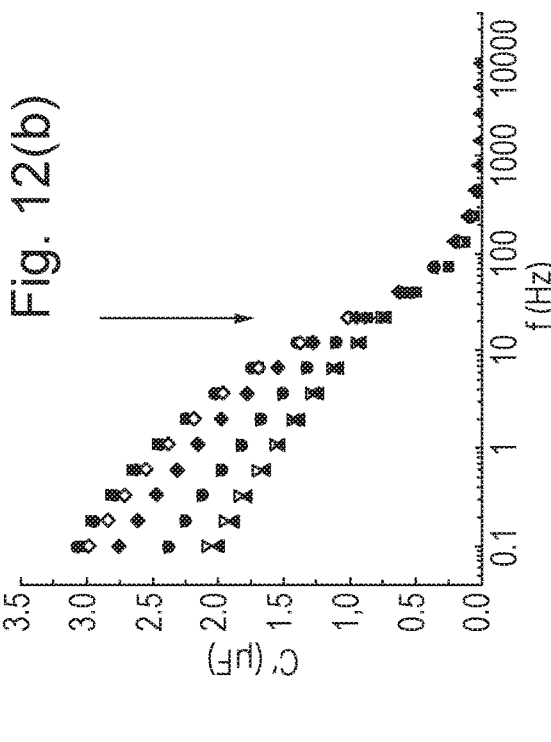
FIG. 12 shows redox capacitive data for anti-CRP/PANI-10 min after exposure to increasing concentrations of CRP in 1% FBS, as described in Example 1: panel a) shows capacitive Nyquist plots, with the eight traces corresponding, from that with highest maximum value to that with lowest maximum value, to analyte (antigen) concentrations of 0, 0.25, 0.5, 1, 2, 4, 8 and 16 μm/mL concentration, respectively; panels b) and c) show Bode plots of the real and imaginary capacitance, respectively, with the eight traces in each panel corresponding, from that with highest maximum value to that with lowest maximum value, to analyte (antigen) concentrations of 0, 0.25, 0.5, 1, 2, 4, 8 and 16 μm/mL concentration, respectively; and panel d) shows a slope of the linear region of the calibration curve (sensitivity) as a function of polymerization time (top trace shows slopes of calibration curved obtained for CRP in fetal bovine serum (FBS) 1%, while bottom trace shows slopes of calibration curved obtained for CRP in Phosphate buffer (PB)).
Figure 12B:
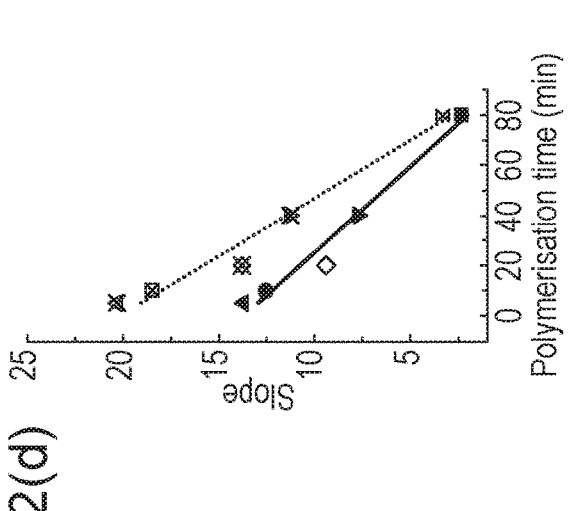
Figure 12C:
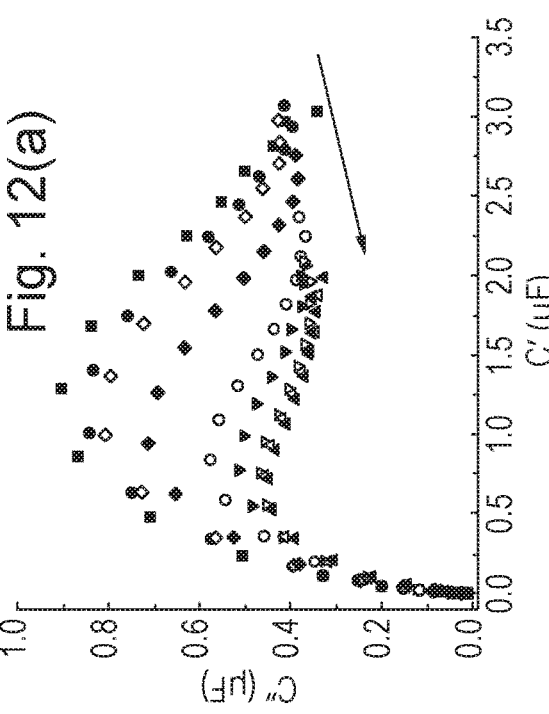
Figure 12D:
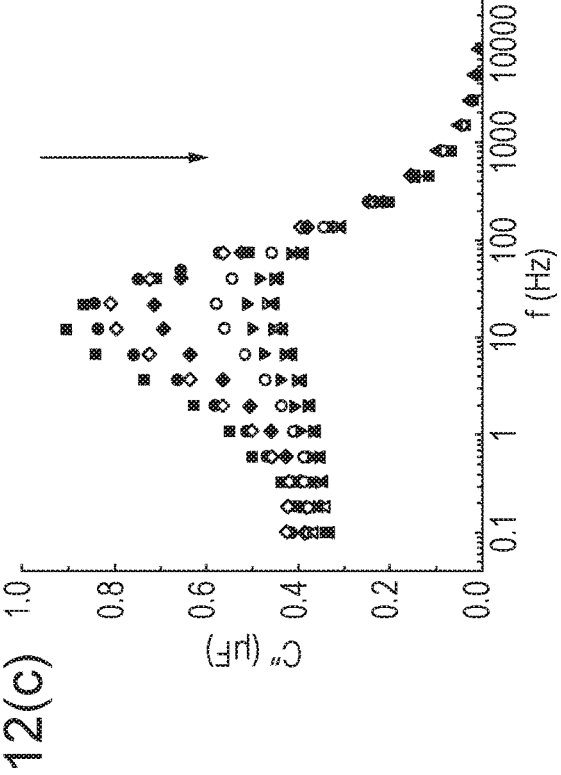

The subsequent response of these anti-CRP modified PANI interfaces towards CRP in PB could be accurately described by a Langmuir-Freundlich adsorption isotherm (FIG. 11, panel a)). The sensitivity of the sensor (as determined by the slope of the linear region in the calibration curve) decreases with increasing PANI coverage, as shown in FIG. 12). This was attributed to an enhanced receptor-to-transducer ratio in the thinner films (the quantified antibody loading is constant within error, across different film thicknesses). If one assumes that only the outer periphery of the film is functionalized with the receptor, then thicker films will be associated with a greater proportion of redox charging entities more remote from the recognition process (and presumably less sensitive to it).

The optimal balance of sensitivity and fouling was observed for PANI-10 min and this interface found to respond selectively to CRP in dilute serum with a response accurately described by a Langmuir-Freundlich adsorption isotherm ($R^2$=0.9995), with a $K_d$ of 19 nM, n=2.1 (indicative of a somewhat heterogeneous interface) and a maximum relative response of 38%. Over a linear range from 0.25-2 µg/mL this corresponds to a sensitivity of 24%/decade, significantly higher than that attainable for a previously reported Fc-SAM-based CRP sensor operating in pure buffer (Piccoli et al. Anal. Chem. 2018, 90 (5), 3005-3008). These PANI-PA interfaces enabled CRP detection across the whole clinical range, with a LOD of 0.5 µg/mL (4.5 nM).

Interfacial specificity was assessed by exposure to fibrinogen from human plasma (100 µg/mL) and human serum albumin (100 µg/mL), whereby a negligible response (≤2%) was observed. In swapping out the anti-CRP anti-body for anti-D-dimer, good selectivity for this second cardiac marker is resolved (FIG. 11, panel b)).

Conclusions

In summary, this example describes a redox capacitive biosensor based on a phytic acid-doped PANI polymer. This redox active support displayed excellent baseline stability (≤2% drift over 7 h after an initial stabilization over 30 min) and showed, without any further integration of anti-fouling components, a good resistance to non-specific protein adsorption. The redox charging features (scale and timeframe) are tunable through film thickness and enable a tuning of the sensitivity of the interface. The subsequent facile integration of a high antibody load generates interfaces of good target specificity. At optimal redox charging: receptor ratios a selective assaying of the cardiac biomarker CRP was possible across its entire clinically relevant range and down to 0.5 µg/mL. The electropolymerisation assembly is believed to be readily translatable to any conductive surface (and any biomarker of interest).

Example 2

In this example an impedance-derived capacitance method is shown to able to cleanly resolve the resonant conductance characteristics of an electrode-confined polymer film. In decorating the film with receptors, this conductance is thereafter modulated by the capturing of specific targets, demonstrated herein with C-reactive protein. This entirely reagentless and single step marker quantification is relevant to the drive of moving assays to a scaleable format requiring minimal user intervention.

Introduction

The electrochemical capacitance $C_\mu$ (also referred to herein as Cr) is mesoscopic in essence and related to the redox density-of-states (DOS) of film-confined redox addressable functionalities. In this example, it is shown that resonant conductance of the film associated to the redox capacitive states can also be used to transduce local binding events in an entirely "reagentless" manner.

In order to charge/discharge electrode-confined redox states, such as those presented by a faradaically-active polymer film, they must be electronically addressable from the electrode such that the imposition of a specific dV promotes a resonant exchange of electrons. If a sinusoidal wave is superimposed on this bias the interfacial capacitance is readily mapped, as is the conductance across the "molecular bridge" spanning the space between electrode and redox site. The chemical potential of this bridge is related to the potential gradient through $dV=-d\mu/e$, where e is the elementary charge. For an ideal quantum mechanical single electrical channel, the current is $di=-d\mu(ev/L)(\delta N/\delta\mu)$, where N is the number of electrons, and v the charge velocity component along the channel length L. Importantly, in this mesoscopic regime of scale, the "bridge" electronic properties show a dependency on the bridge DOS through $(\delta N/\delta\mu)=2 L/hv$ (h is the Planck constant). This DOS is, in turn, spatially and energetically coupled to that of the (faradaically charging) redox sites in a manner that governs the charge and discharge characteristics of the film, where the associated electric current can be expressed as $di=N(2e^2/h)dV$. Consequently, one can write $i=NG_0V$, where $NG_0=2Ne^2/h$ and $G_0=2e^2/h$ is the quantum of conductance. For a (realistic) transmittance through multiple channels, the arising mesoscopic conductance G is given by $G=G_0\Sigma_n T_n(\mu)=NG_0$, where $\Sigma_n T_n(\mu)$ represents the overall transmission probability across the "molecular bridge" and equates to N if the transmittance of the individual channels is ideal. A key part of this formalism, is that any change in $C_\mu$ (such as that induced by a local target capture event) will alter the mesoscopic conductance G of the bridge.

Figure 13A:
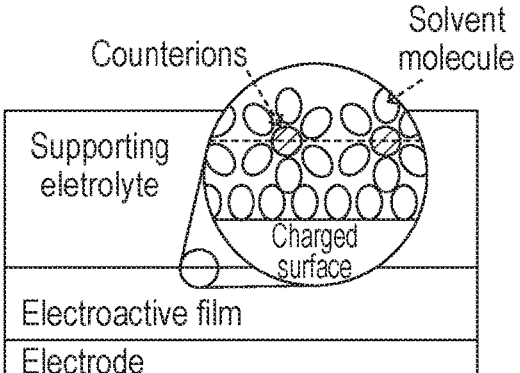
FIG. 13 shows that, for a charged electrode-modified electroactive film immersed in a supporting electrolyte (a) the electrochemical features of the interface can be modelled by an equivalent circuit comprising solution resistance $R_s$ connected in series with a parallel combination of the $C_{dl}$ and $R_q$ in series with $C_\mu$ (b). A typical impedance Nyquist diagram is shown in (c), which can be usefully transformed into capacitance domain (d). $R_s$ can be obtained at high frequencies ($\omega = 2\pi f$), as shown in (c) $C_\mu$ can be then estimated by the diameter of the semicircle. (e) Bode plot for the imaginary part of the capacitance as the function of frequency. The peak frequency $f_q$ can be used to estimate $R_q$.
Figure 13B:
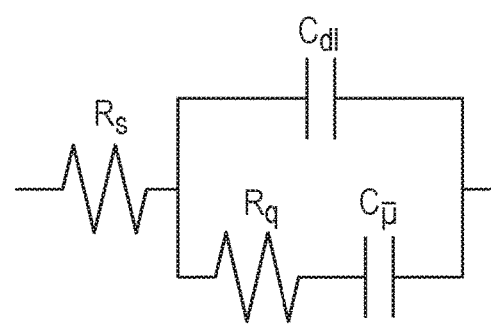
Figure 13C:
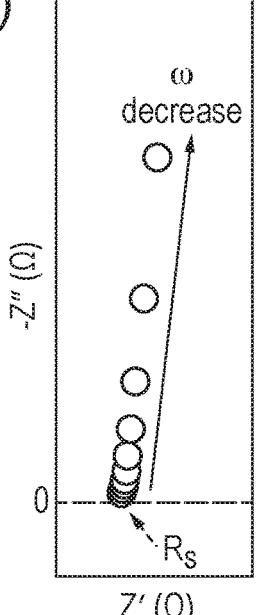
Figure 13D:
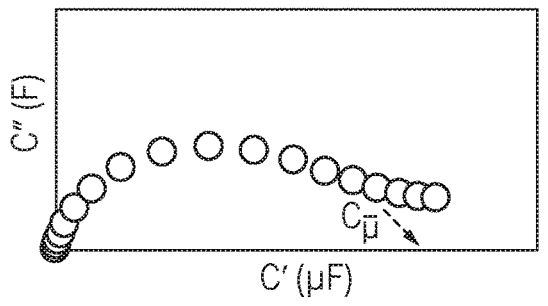
Figure 13E:
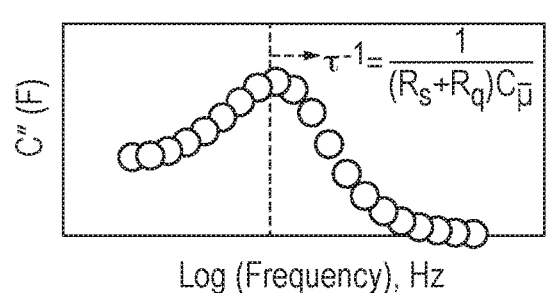

Traditional EIS, encompassing an analysis of the charge transfer between electrode and free species in solution (in parallel to double layer capacitance), does not report on resonant conductance/resistance because the latter exists only when molecules or films are physically or chemically attached to the electrode. Even in the absence of a traditional solution phase redox probe, a standard impedimetric Nyquist analysis of an electrode coupled conductive film fails to resolve any meaningful film resistance (FIG. 13c; where only solution resistance, $R_s$, is resolvable). For this we revert to a capacitance analysis. We note first that $C_\mu$ is given by the diameter of a capacitive Nyquist semicircle (FIG. 13d) and that $C_\mu$ dominates over $C_{dl}$, for redox addressable films (where the double layer charging is heavily suppressed). The resistive component of the charging element $R_q$ is accessed through a Bode analysis noting that $\tau^{-1}=1/(R_s+R_q)C_\mu$, where this inverse results in a RC timeconstant corresponds to the peak frequency $f_p=1/(2\pi\tau)$ (FIG. 13e). Film conductance is $G=1/R_q$. This $R_q$, recorded when film redox states are resonant with electrode states, corresponds to the higher limit of the conductance (FIG. 14b), but can thereafter be modulated by any change in bridge chemical potential; these changes are induced by localised (recognition) effects at the electronically coupled redox sites.

In prior work it has been demonstrated that the capacitive analysis of redox addressable and target receptive films can be applied in signal transduction, and that there is an intrinsic association between resolved molecular film capacitance and film conductance (see, for instance, Example 1). In this example, it is shown that, with suitably prepared conductive polymer films, the recruitment of targets is associated with a measurable change in film chemical potential and thus conductance. Such "conductometric" analyses have classically been restricted to FET configurations. Although these possess an inherent amplification, they also require very substantial control over microfabrication and can be problematic to reproducibly scale. The conductance analyses herein are "single electrode contact" in basis and very readily scaled. We exemplify this here with a redox charging conductive polyaniline film and a quantification of C-reactive protein biomarker (CRP), a cardiac, acute phase and inflammatory marker.

EXPERIMENTAL

General

Screen printed electrodes were prepared using a graphene nanoplate ink (obtained from HDPlas). The screen-printed electrodes were used in an array of 5 working electrodes with a diameter of 0.7 mm. CRP and anti-CRP were purchased from Biorad, UK. Aniline and phytic acid (PA) were obtained from Sigma Aldrich. Ultrapure water was used in all solutions and obtained from a Milli-Q system. Phosphate buffer (PB, 0.1 M), pH=7.4 was prepared by mixing 0.2 M $NaH_2PO_4$ and 0.2 M $Na_2HPO_4$ stock solutions to give pH 7.4 and subsequent dilution to 0.1 M.

Electrochemical Analyses

All electrochemical experiments were performed with a portable PalmSens potentiostat in a three-electrode configuration, consisting of a screen-printed graphene nanoplate working electrode (SPE), a screen-printed silver reference electrode, and a screen-printed gold counter electrode. All experiments were performed in 0.1 M phosphate buffer (PB), pH 7.4, unless otherwise stated.

EIS was performed between 9 kHz to 0.1 Hz (20 frequencies logarithmic arranged), with a sigmoidal AC perturbation of 10 mV (peak-to-peak). These experiments were performed at DC "redox-in" or formal potential of PANI film (p–0.2 V). Impedance-derived capacitance spectroscopic was obtained via $C'(\omega)=Z''/\omega|Z|^2$ and $C''(\omega)=Z'/\omega|Z|^2$, where $\omega$ is the angular frequency ($\omega=2\pi f$). The $C_\mu$ of the interface was obtained graphically as the diameter of the semicircle of the capacitive Nyquist plots. The conductance G was calculated from the resistance $R_q$ determined from the peak frequency $f_p$ of the imaginary capacitance Bode plot $(\tau^{-1}=1/[(R_s+R_q)C_\mu]=2\pi f_p)$ as shown in FIG. 13*e* as example). Note that $G=1/R_q$, and that additionally $R_s$ can be obtained from the impedimetric Nyquist plot at high frequencies region (as shown in FIG. 13*c*). The relative response RR (%) for the signal transduction S was obtained as follows $RR(\%)=S_{[target]}-S_{blank}/S_{blank}$, where $S_{[target]}$ is the signal transduction for a certain target concentration, and $S_{blank}$ is the signal of the blank. As signal transduction S we used G. The limit of detection (LOD) of the assay was determined according to LOD=$3\sigma$/slope, where $\sigma$ is the standard deviation of the y-intercept of the standard plot (RR(%) versus target concentration).

Sensor Interface Generation

Electrodes were washed with copious amounts of water, followed by electrochemical polishing in 0.1 M KOH, between −1.0 V to 1.3 V for 20 cycles. Electropolymerisation of pythic acid doped polyaniline (PANI-PA) was performed in an aqueous solution of 1 mL 98% aniline and 2 mL of 50% phytic acid (w/w in H2O) with the addition of 17 mL of MilliQ water by applying a current density of 10 μA/cm2 for 10 min. The film was rinsed with 0.1 M PB and then equilibrated in the same buffer for 10 min before further electrochemical characterization. Covalent immobilization of the receptor was performed by exposure of the PANI-PA films to 2.5% glutaraldehyde (in PB) for 30 min, followed by rinsing with copious amounts of PB and exposure to 5 μg mL-1 of anti-CRP or 5 μg mL-1 anti-D-dimer for 30 min. After rinsing with 0.1 M PB (pH 7.4), remaining active sites were deactivated with 10 mM ethanolamine in 0.1 M PB (pH 7.4) for 30 min, followed by rinsing with PB.

Immunoassay

Sensor surfaces were first equilibrated in PB for 30 min. Prior to a ten-minute exposure to defined concentrations of target marker (or control) spiked into 1% fetal bovine serum (FBS). Sensors were then rinsed in PB and $C_\mu$, $\tau$, and $R_s$ recorded in pure PB in order to obtain conductance of the film for each target concentration.

Results and Discussion

Figure 14A:
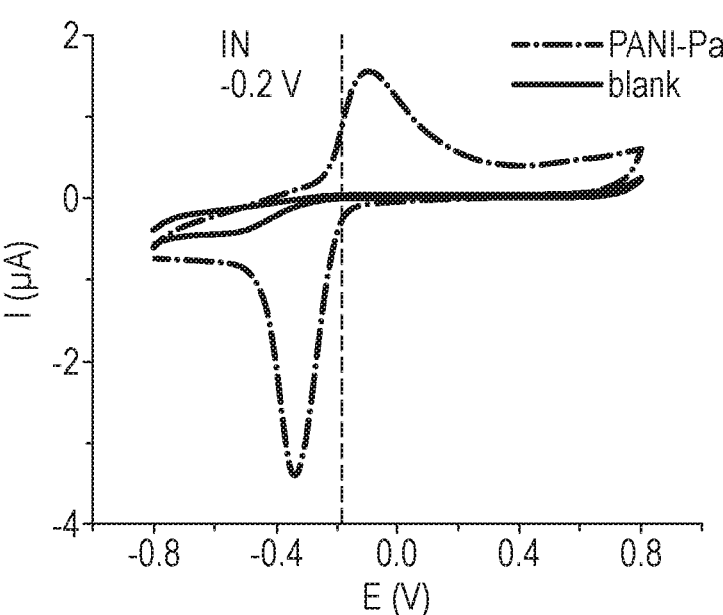
FIG. 14 shows (a) CV at 100 mV s-1 before (blank; black line) and after electropolymerisation of PANI-PA (grey line) in 0.1 M PB, showing the formal potential at −0.2 V ("IN" denoting inside the faradaic window); and (b) Nyquist plots of capacitance before (black) and after (grey) electropolymerisation of PANI-PA, measured at the formal potential. The diameter of semicircle corresponds to $C_\mu$.
Figure 14B:
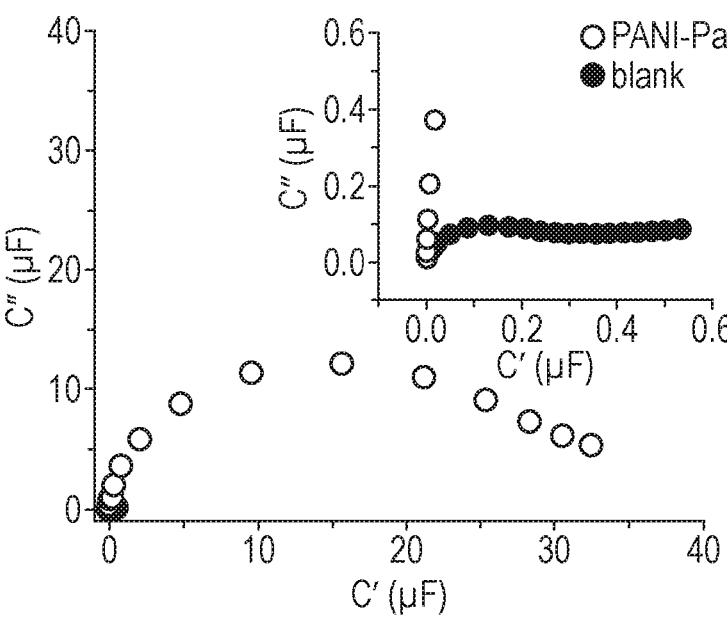

In generating antibody supporting conductive films, aqueous phase electrodeposition generates a stable electroactive film presenting an oxidation potential peak ($V_{ox}$) at about −0.15 V, and reduction potential peak ($V_{red}$) at about −0.25 V in PB solution (FIG. 14*a*). $C_\mu$ is resolved to be, as expected, maximal at the electrochemical formal potential (~32 μF from the semicircle diameter in FIG. 14*b*). In the absence of PANI a resolved (geometric) double layer capacitance is ~0.3 μF.

Figure 15A:
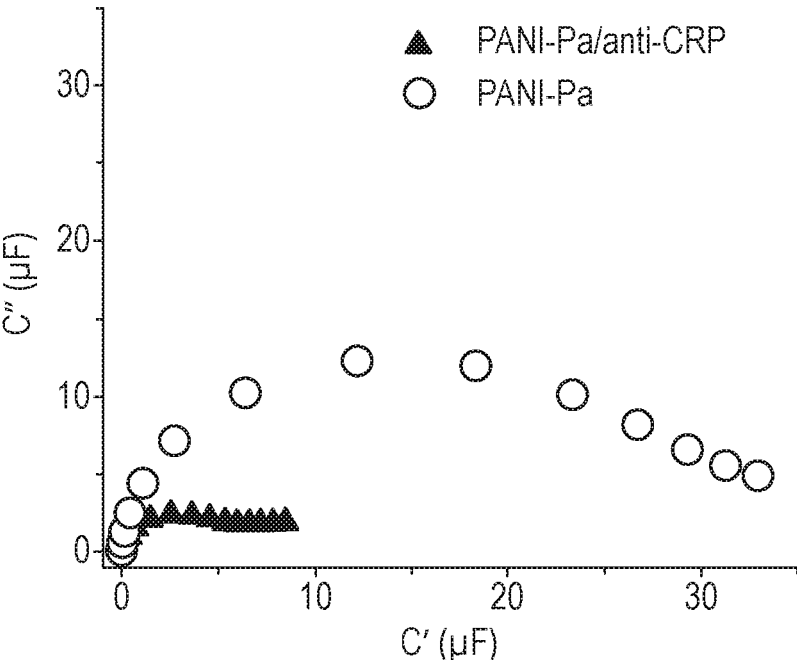
FIG. 15 shows (a) Capacitive Nyquist plots recorder at PANI-PA formal potential before (circle) and after (triangles) anti-CRP immobilization using glutaraldehyde cross-link agent. The shift observed in redox capacitance signal after antibody immobilization on PANI-Pa film is about −75%, shown in (b), evidencing antibody attachment.
Figure 15B:
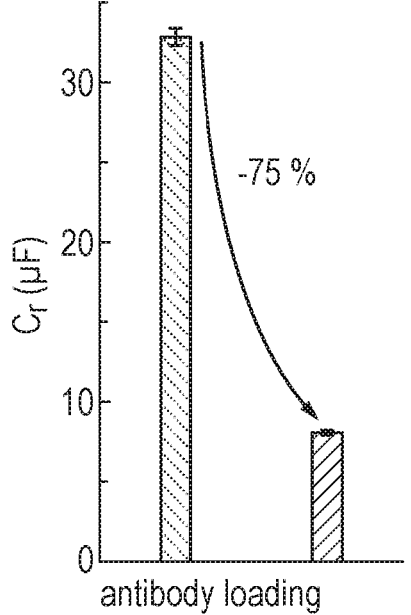
Figures 16A, 16B, 16C, 16D:
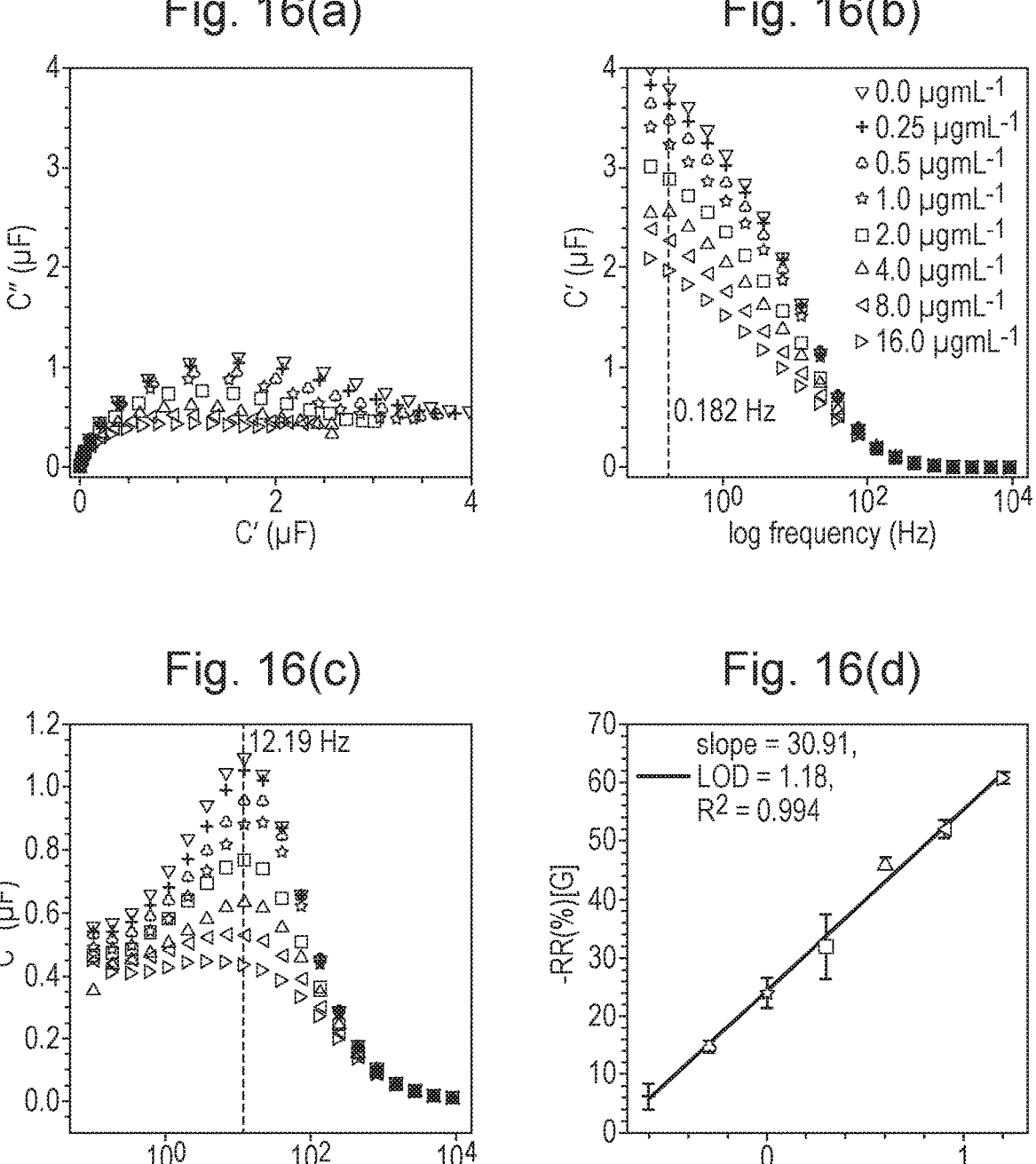
FIG. 16 shows (a) Capacitance Nyquist plots, (b) real C' and (c) C'' imaginary component of complex capacitance vs. frequency (Bode plots) after sensor exposure to CRP in 1% fetal bovine serum. The conductance G is related to C'' such as G=ωC'' in units of Siemens. (d) Calibration curves are obtained from transduction signal using G as shown in Table SI-2.1 at SI. The slope (sensitivity) and LOD values are shown in the plot (R2=0.994). Error bars represent standard deviation from independent measurements.

A subsequent standard glutaraldehyde coupling of anti-CRP results in a decrease in $C_\mu$ (FIG. 15), related to the attenuation of the redox signal as expected. In more detail, anti-CR was immobilized by glutaraldehyde protocol and, after CRP attachment, a decrease in electrochemical capacitance $C_\mu$ of about 75% was observed. This change is concordance with previously redox-capacitance works which a decrease in capacitance signal is obtained after protein binding. As shown in FIGS. 16*a* and 16*b*, $C_\mu$ thereafter decreases as target concentrations increases (visualized at ~18 mHz, the frequency where the real component of the complex capacitance produces the hemisphere from which $C_\mu$ is obtained). By condensing the circuit elements from the Nyquist and Bode capacitive plots (see above for details or FIG. 16 and also Table 3), film conductance can be resolved to decrease on specific target recruitment. This conductance decrease/resistance increase is consistent with the observed decrease in coupled electrochemical capacitance (FIG. 15*a*) which in turn directly reflects the current through the "bridge", noting that di=−dμ(ev/L)(δN/δμ), where δN/δμ is DOS.

TABLE 3

| Circuit elements estimation. The values are represented as the mean ± standard deviation for N = 3. | | | |
|---|---|---|---|
| [CRP] μg mL⁻¹ | Rs (kΩ) | $C_\mu$ (μF) | $R_q$ (kΩ) | G (μS) |
| Blank | 1.58 ± 0.02 | 3.78 ± 0.03 | 1.88 ± 0.02 | 531 ± 5 |
| 0.25 | 1.58 ± 0.01 | 3.63 ± 0.06 | 2.01 ± 0.06 | 498 ± 15 |
| 0.50 | 1.55 ± 0.01 | 3.47 ± 0.04 | 2.21 ± 0.03 | 453 ± 6 |
| 1.00 | 1.57 ± 0.01 | 3.23 ± 0.05 | 2.48 ± 0.07 | 404 ± 12 |
| 2.00 | 1.74 ± 0.14 | 2.89 ± 0.04 | 2.78 ± 0.21 | 361 ± 26 |
| 4.00 | 1.56 ± 0.01 | 2.57 ± 0.04 | 3.51 ± 0.09 | 285 ± 7 |
| 8.00 | 1.82 ± 0.01 | 2.27 ± 0.04 | 3.93 ± 0.11 | 254 ± 7 |
| 16.00 | 1.80 ± 0.01 | 1.97 ± 0.03 | 4.81 ± 0.07 | 208 ± 3 |

Figure 17A:
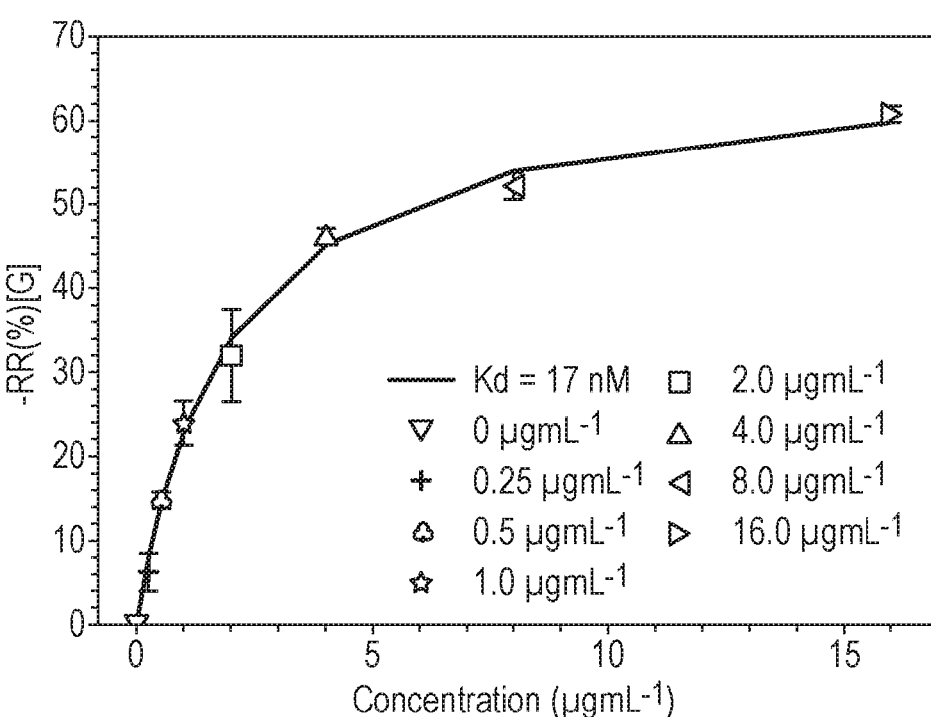
FIG. 17 shows (a) Relative response of the conductance (−RR, %) for anti-CRP interface for different target concentration diluted in 1% FBS. The response was fitted using Langmuir isotherm, presenting $R^2$–0.994 with a $k_d$=17 nM. (b) Negative control and selectivity assay by exposing anti-CRP or anti-D-dimer interface to 2 μg/mL of CRP (left bars) or D-dimer (right bars) in 1% FBS. Error bars represent standard deviation from independent measurements.
Figure 17B:
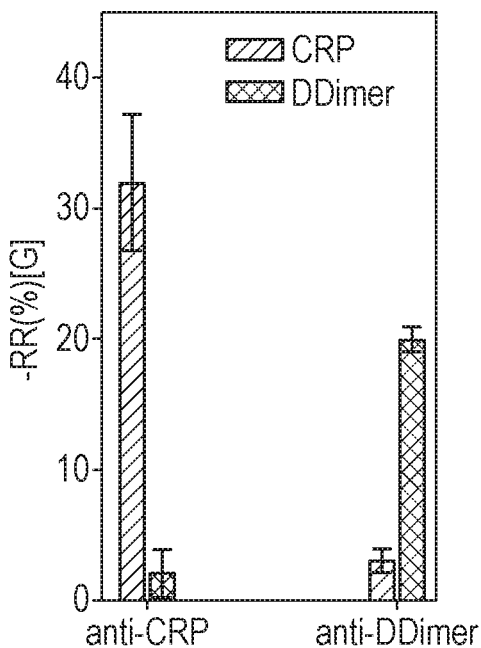

A plot of interfacial relative response (RR, %; (see above for details) generates a standard curve (FIG. 16*d*), with a resolved sensitivity of ~30% per decade, higher than that typically reported for capacitance sensors and a detection limit (1 μg mL−1/10 nmol L−1) that is clinically relevant. Interfacial conductance responses show good levels of selectivity (FIG. 17*b*) and can be accurately ($R^2>0.99$) described by the Langmuir-type isotherm plot (FIG. 17*a*), with a dissociation constant entirely consistent with previous reports.

Conclusion

It has been shown that the conductance of an electrode-confined redox polymer can be used as a transducer signal for biosensing. This conductance is directly correlated to the electrochemical or redox capacitance of the film that arises from its embedded faradaically-active sites. These principles represent a highly accessible, readily scaleable, single electrode contact, field effect sensing ability.

The invention claimed is:

1. An electrochemical method of sensing a target species, which method comprises:
   (A) contacting a carrier medium that may comprise said target species with an electrode that comprises:
      (i) an electrically conductive substrate;
      (ii) a film comprising a redox-active, electrically conductive polymer disposed on the substrate, wherein the redox-active, electrically conductive polymer is polyaniline (PANI) and wherein the film is doped with phytic acid; and
      iii) at least one receptor associated with the film, wherein the receptor is capable of binding to the target species; and
   (B) determining, via electrochemical capacitance spectroscopy, whether the target species is present in the carrier medium.

2. The method of claim 1, wherein:
   (i) the redox-active, electrically conductive polymer is PANI and comprises a plurality of redox active monomeric repeating units which are aniline units; and
   (ii) a surface coverage of said plurality of redox active monomeric repeating units on the electrically conductive substrate is from 3 to 40 nmolcm⁻², as measured from a redox capacitance, Cr, of the electrode obtained via circuit fitting and in the presence of a control carrier medium containing no target species.

3. The method of claim 1, wherein the receptor is selected from the group consisting of aptamers, antibodies, antibody fragments, oligosaccharides, peptides and proteins.

4. The method of claim 1, wherein the receptor is an aptamer.

5. The method of claim 1, wherein the electrically conductive substrate is a gold substrate.

6. The method of claim 1, wherein the electrically conductive substrate is not a gold substrate.

7. The method of claim 1, wherein the electrically conductive substrate comprises carbon, platinum, silver, ruthenium oxide or indium tin oxide (ITO).

8. The method of claim 1, wherein the electrically conductive substrate is a screen-printed electrode (SPE) substrate.

9. The method of claim 1, wherein the target species is an antigen or analyte selected from the group consisting of dengue NS1 protein; angiotensin I converting enzyme (peptidyl-dipeptidase A); adiponectin; advanced glycosylation end product-specific receptor; alpha-2-HS-glycoprotein; angiogenin, ribonuclease, RNase A family, 5; apolipoprotein A-1; apolipoprotein B (including Ag (x) antigen); apolipoprotein E; BCL2-associated X protein; B-cell CLL/lymphoma 2; complement C3; chemokine (C-C motif) ligand 2; CD 14, soluble; CD 40, soluble; cdk5; pentraxin-related; cathepsin B; dipeptidyl peptidase IV; Epidermal growth factor; endoglin; Fas; fibrinogen; ferritin; growth hormone 1; alanine aminotransferase; hepatocyte growth factor; haptoglobin; heat shock 70 kDa protein 1 B; intercellular adhesion molecule 1; insulin-like growth factor 1 (somatomedin C); insulin-like growth factor 1 receptor; insulin-like growth factor binding protein 1; insulin-like growth factor binding protein 2; insulin-like growth factor-binding protein 3; interleukin 18; interleukin 2 receptor, alpha; interleukin 2 receptor, beta; interleukin 6 (interferon, beta 2); interleukin 6 receptor; interleukin 6 signal transducer (gp130, oncostatin M receptor); interleukin 8; activin A; leptin (obesity homolog, mouse); plasminogen activator, tissue; proopiomelanocortin (adrenocorticotropin/beta-lipotropin/alpha-melanocyte stimulating hormone/beta-melanocyte stimulating hormone/beta-endorphin); proinsulin; resistin; selectin e (endothelial adhesion molecule 1); selectin P (granule membrane protein 140 kDa, antigen CD62); serpin peptidase inhibitor, clade E (nexin, plasminogen activator inhibitor type 1), member 1; serum/glucocorticoid regulated kinase; sex hormone-binding globulin; transforming growth factor, beta 1 (Camurati-Engelmann disease); TIMP metallopeptidase inhibitor 2; tumor necrosis factor receptor superfamily, member 1 B; vascular cell adhesion molecule 1 (VCAM-1); vascular endothelial growth factor; Factor II, Factor V, Factor VIII, Factor IX, Factor XI, Factor XII, F/fibrin degradation products, thrombin-antithrombin III complex, fibrinogen, plasminogen, prothrombin, and von Willebrand factor and the like, Markers useful for diabetes include for example C-reactive protein; glucose; insulin; TRIG; GPT; HSPA1 B; IGFBP2; LEP; ADIPOQ; CCL2; ENG; HP; IL2RA; SCp; SHBG; and TIMP2.

10. The method of claim 1, wherein step (B) comprises determining a concentration of the target species.

11. The method of claim 1, wherein the electrochemical capacitance spectroscopy comprises determining a conductance of the electrode.

12. The method of claim 11, wherein said determining, via electrochemical capacitance spectroscopy, comprises:

(B)(i) obtaining a measurement of the conductance of the electrode when in contact with the carrier medium that may comprise said target species; and (B)(ii) comparing said measurement with the conductance of the electrode when in contact with a reference carrier medium that does not comprise said target species.

13. The method of claim 1, wherein said determining, via electrochemical capacitance spectroscopy, comprises:

(B)(i) obtaining a measurement of a redox capacitance of the electrode when in contact with the carrier medium that may comprise said target species; and (B)(ii) comparing said measurement with the redox capacitance of the electrode when in contact with a reference carrier medium that does not comprise said target species.

14. An electrochemical method of sensing a target species, which method comprises:

(A) contacting a carrier medium that may comprise said target species with an electrode that comprises:

(i) an electrically conductive substrate;

(ii) a film comprising a redox-active, electrically conductive polymer disposed on the substrate, wherein the redox-active, electrically conductive polymer is polyaniline (PANI) and wherein the film is doped with phytic acid; and (iii) at least one receptor associated with the film, wherein the receptor is capable of binding to the target species; and (B) determining, via electrochemically determining a conductance of the electrode, whether the target species is present in the carrier medium.

* * * * *